(12) United States Patent
Brown et al.

(10) Patent No.: US 8,211,113 B2
(45) Date of Patent: Jul. 3, 2012

(54) PROSTHESIS CUTTING GUIDE, CUTTING TOOL AND METHOD

(75) Inventors: Scott Brown, Warsaw, IN (US); Jim Rogers, Warsaw, IN (US); Alan C. Merchant, Mountain View, CA (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/176,891

(22) Filed: Jun. 21, 2002

(65) Prior Publication Data

US 2003/0236521 A1 Dec. 25, 2003

(51) Int. Cl.
*A61B 17/60* (2006.01)
*A61F 2/00* (2006.01)

(52) U.S. Cl. ......................................... 606/96
(58) Field of Classification Search ............... 606/53, 606/79, 80, 81, 82, 86, 87, 88, 89, 96, 97, 606/98; 33/512, 562, 563, 564, 565, 566; 144/144.51, 144.1, 137; 409/178, 179
See application file for complete search history.

(56) References Cited

U.S. PATENT DOCUMENTS

| | | | |
|---|---|---|---|
| 1,723,517 A * | 8/1929 | McFadden | ............ 33/474 |
| 3,820,167 A | 6/1974 | Sivash | |
| 3,855,638 A | 12/1974 | Pilliar | |
| 3,943,576 A | 3/1976 | Sivash | |
| 3,996,625 A | 12/1976 | Noiles | |
| 4,077,070 A | 3/1978 | Sivash | |
| 4,524,766 A | 6/1985 | Petersen | |
| 4,530,114 A | 7/1985 | Tepic | |
| 4,551,863 A | 11/1985 | Murray | |
| 4,567,885 A * | 2/1986 | Androphy | ............ 606/88 |
| 4,703,751 A * | 11/1987 | Pohl | ............ 606/62 |
| 4,721,104 A * | 1/1988 | Kaufman et al. | ............ 606/88 |
| 4,784,126 A * | 11/1988 | Hourahane | ............ 606/60 |
| 4,790,852 A | 12/1988 | Noiles | |
| 4,846,839 A | 7/1989 | Noiles | |
| 4,865,603 A | 9/1989 | Noiles | |
| 5,011,496 A | 4/1991 | Forte et al. | |
| 5,035,699 A | 7/1991 | Coates | |
| 5,053,037 A * | 10/1991 | Lackey | ............ 606/79 |
| 5,122,144 A * | 6/1992 | Bert et al. | ............ 606/88 |
| 5,167,619 A | 12/1992 | Wuchinich | |
| 5,190,547 A | 3/1993 | Barber, Jr. et al. | |
| 5,246,444 A * | 9/1993 | Schreiber | ............ 606/87 |
| 5,282,803 A * | 2/1994 | Lackey | ............ 606/80 |
| 5,295,992 A | 3/1994 | Cameron | |
| 5,312,411 A * | 5/1994 | Steele et al. | ............ 606/88 |
| 5,326,365 A | 7/1994 | Alvine | |
| 5,344,423 A * | 9/1994 | Dietz et al. | ............ 606/87 |

(Continued)

FOREIGN PATENT DOCUMENTS

EP 0327249 A 8/1989

(Continued)

*Primary Examiner* — Anu Ramana
(74) *Attorney, Agent, or Firm* — Maginot, Moore & Beck, LLP

(57) ABSTRACT

A kit (10) for removal of bone (12) from a patient to prepare a bone cavity (14) for receiving a joint prosthesis (16) is provided. The kit (10) includes a guide (20) for cooperation with the bone (12) and a rotatable tool (22). The tool (22) is constrainable by the guide (20) for removal of the bone (12). The guide (20) includes a first portion (24) thereof cooperable with the tool (22) and a second portion (24) thereof cooperable with the bone (12).

25 Claims, 25 Drawing Sheets

U.S. PATENT DOCUMENTS

| | | | | |
|---|---|---|---|---|
| 5,364,402 A | * | 11/1994 | Mumme et al. | 606/88 |
| 5,409,489 A | | 4/1995 | Sioufi | |
| 5,454,816 A | * | 10/1995 | Ashby | 606/88 |
| 5,534,005 A | | 7/1996 | Tokish, Jr. et al. | |
| 5,540,692 A | | 7/1996 | Tidwell | |
| 5,571,110 A | | 11/1996 | Matsen, III et al. | |
| 5,593,411 A | * | 1/1997 | Stalcup et al. | 606/88 |
| 5,601,563 A | * | 2/1997 | Burke et al. | 606/86 R |
| 5,613,970 A | * | 3/1997 | Houston et al. | 606/88 |
| 5,624,443 A | | 4/1997 | Burke | |
| 5,624,463 A | * | 4/1997 | Stone et al. | 623/23.61 |
| 5,634,927 A | * | 6/1997 | Houston et al. | 606/96 |
| 5,683,397 A | * | 11/1997 | Vendrely et al. | 606/88 |
| 5,743,910 A | | 4/1998 | Bays et al. | |
| 5,766,259 A | | 6/1998 | Sammarco | |
| 5,916,220 A | * | 6/1999 | Masini | 606/88 |
| 5,925,049 A | * | 7/1999 | Gustilo et al. | 606/82 |
| 6,106,529 A | | 8/2000 | Techiera | |
| 6,193,723 B1 | | 2/2001 | Cripe et al. | |
| 6,277,121 B1 | | 8/2001 | Burkinshaw et al. | |
| 6,321,457 B1 | * | 11/2001 | Lariviere et al. | 33/562 |
| 6,342,057 B1 | * | 1/2002 | Brace et al. | 606/96 |
| 6,355,045 B1 | * | 3/2002 | Gundlapalli et al. | 606/88 |
| 6,488,687 B1 | * | 12/2002 | Masini | 606/88 |
| 6,554,837 B1 | * | 4/2003 | Hauri et al. | 606/87 |
| 6,554,838 B2 | * | 4/2003 | McGovern et al. | 606/87 |

FOREIGN PATENT DOCUMENTS

| | | |
|---|---|---|
| EP | 0 327 249 A1 | 6/1992 |
| EP | 0 682 916 B1 | 11/1995 |
| FR | 2 616 059 A1 | 12/1988 |
| WO | 94/05211 A1 | 3/1994 |

\* cited by examiner

PROSTHESIS CUTTING GUIDE, CUTTING TOOL AND METHOD

CROSS-REFERENCE TO RELATED APPLICATIONS

Cross reference is made to the following applications: U.S. patent application Ser. No. 10/177,966 entitled "PROSTHESIS CAVITY CUTTING GUIDE, CUTTING TOOL & METHOD" and U.S. patent application Ser. No. 10/176,934 entitled "PROSTHESIS REMOVAL CUTTING GUIDE, CUTTING TOOL AND METHOD" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Joint replacement surgery is quite common and it enables many individuals to function properly when it would not otherwise be possible to do so. Such patients of joint replacement surgery typically suffer from osteoarthritis or rheumatoid arthritis. Artificial joints usually comprise metallic, ceramic and/or plastic components that are fixed to existing bone.

Such joint replacement surgery is otherwise known as total joint arthroplasty. Total joint arthroplasty is a well known surgical procedure by which a diseased and/or damaged joint is replaced with a prosthetic joint. In a typical total joint arthroplasty, the adjacent ends of the bones and cartilage comprising the joint are resected and the artificial implants are secured thereto.

When only one part of the knee joint is damaged, only the damaged compartment is resected and replaced. This is known as a uni-compartmental knee joint arthroplasty.

When only the patellar articular surface and the adjacent groove on the distal end of the femur, the trochlear, with which it articulates, are damaged, replacement of these surfaces is called a patello femoral arthroplasty.

Frequently, when installing the components of the prosthetic joint, cartilage and bone must be resected or removed such that the implanted prosthesis has the same surface profile as the surface prior to its resection. Such arthroplasty thus requires a pocket formed in the bone of a particular shape and depth to provide a location for the prosthesis such that the prosthesis outer-profile replicates that of the pre-resected joint. Among such joints for which a resected pocket is required is a trochlear implant for cooperation with a patella prosthesis for a patello femoral arthroplasty.

The current process for preparing to implant a trochlear prosthesis is to place a template over the femur where the damaged trochlear is located. The trochlear groove of the femur is then physically marked with a tool such as a scribe or marking pen which leaves a mark on the bone or cartilage as the scribe or pen is moved about the periphery of the template. The traced marks on the distal femur serve as a guide for preparing the pocket for the trochlear implant. Osteotomes and hammer plus high-speed rotating burrs are then used to prepare the pocket within the outlined perimeter. This process is very slow and tedious in order to achieve a precise and accurate fit in all dimensions.

A need thus exists for an improved method and instrumentation to assist in the implanting of a trochlear prosthesis or similar implants, which are placed in the bone at a depth to conform to the pre-resected contour of the bone.

SUMMARY OF THE INVENTION

The present invention is directed to a cutting guide, which is utilized with a rotating cutting tool to create pockets at a specific depth in the bone for a trochlear or similar implant. The cutting guide provides an accurate cut both in the outline shape and in the depth of the cut. Additional cutting paths are made inside the outline shape utilizing the cutting tool so that only a minimal amount of material must be removed between the cutting path.

According to one embodiment of the present invention, a kit for removal of cartilage and bone from a patient to prepare a cavity for receiving a joint prosthesis is provided. The kit includes a guide for cooperation with the bone and a rotatable tool. The tool is constrainable by the guide for removal of the bone. The guide includes a first portion thereof cooperable with the tool and a second portion thereof cooperable with the bone.

According to another embodiment of the present invention, a guide is provided for guiding a rotatable tool for removal of cartilage and bone from a patient to prepare a cavity for receiving a joint prosthesis. The guide includes a first portion thereof cooperable with the tool and a second portion cooperable with the bone.

According to yet another embodiment of the present invention, a rotatable tool adapted for removal of cartilage and bone from a patient to prepare a cavity for receiving a joint prosthesis is provided. The tool is constrainable by the guide for removal of the bone.

According to a further embodiment of the present invention, a method for removal of cartilage and bone from a patient to prepare a cavity for receiving a joint prosthesis is provided. The method includes the steps of providing a guide defining an opening therein, exposing a portion of the bone of the patient, placing the guide in cooperation with the bone, providing a tool adapted for cooperation with the opening, inserting the tool at least partially within the opening, causing the tool to move relatively to the guide, and advancing the tool within the opening to form the bone cavity.

The technical advantage of the present invention includes an improved imprint or location of the pocket for the prosthesis. For example, according to one aspect of the present invention, the guide includes channels positioned about the outer periphery of the guide, which conform to the outer periphery of the pocket for placing for a pocket with an outer periphery that is well defined and accurate. Thus, the present invention provides for an improved and accurate location of the pocket for the prosthesis.

Another technical advantage of the present invention includes an improved accuracy in the depth of the pocket into which the implant is to be located. For example, according to one aspect of the present invention, the tool includes a collar, which cooperates with the guide when the tool is placed in the channels of the guide. The collar on the tool seats against the rim around the channels and provides for an accurate and consistent depth of the pocket for the implant.

The technical advantages of the present invention further include the ability to form the pocket for an implant in much greater speed and precision. For example, according to one aspect of the present invention, the guide includes a plurality of spaced apart channels. These channels occupy most of the cross-sectional area of the guide. The guide, in cooperation with the tool, is used to form most of the pocket for the implant. Only a quick and simple use of a small osteotome to remove the small portions of material remaining after the utilization of the burr tool and guide, is required and that can be quickly accomplished. Therefore, with the rapid use of the guide and the burr tool and the minimal use of the osteotome, the pocket may be prepared very quickly and accurately.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 22A; is a plan view of a drill for cooperation with the drill guide of FIG. 22;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
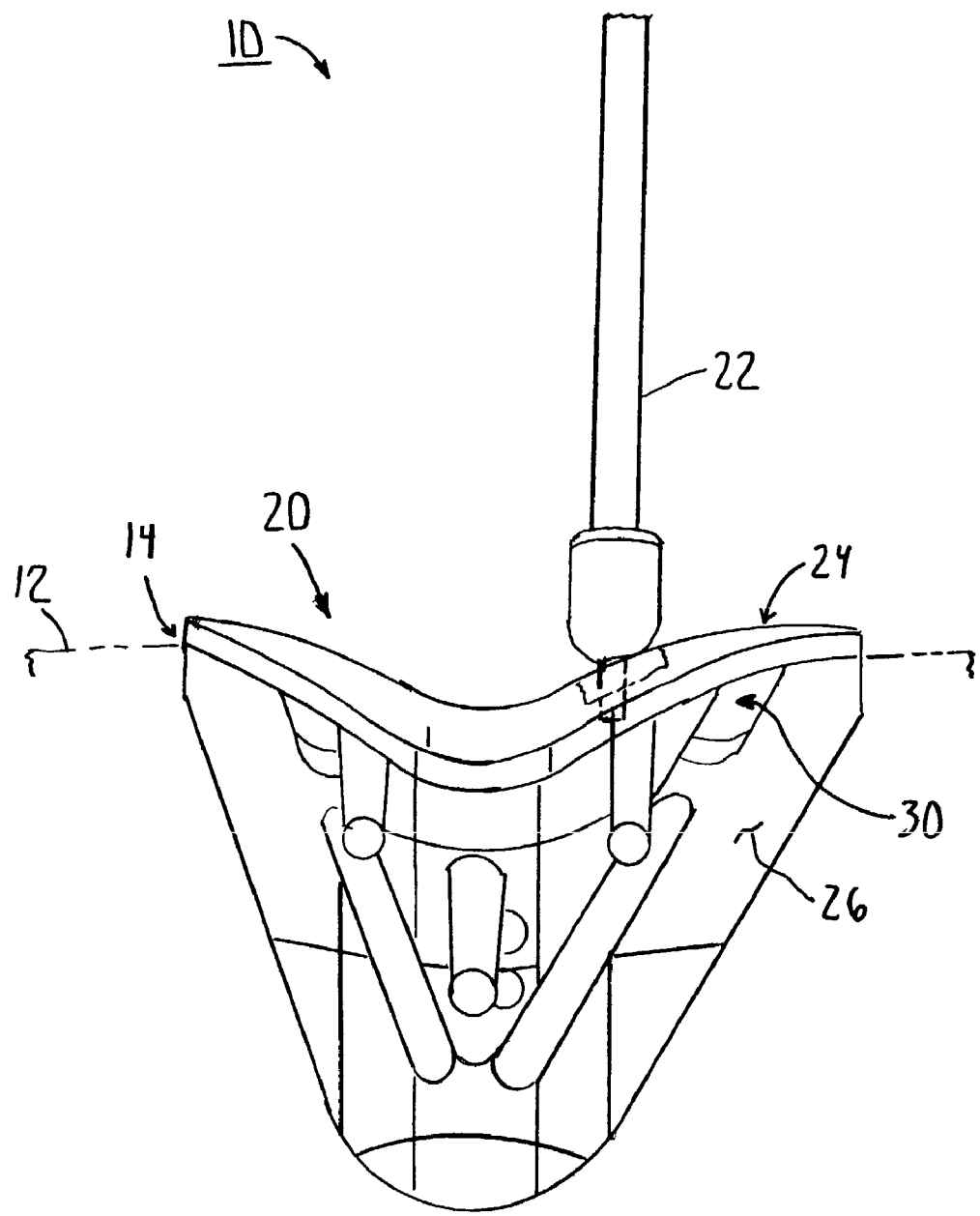
FIG. 1 is a perspective view of a kit according to the present invention including a guide and tool shown in cooperation with each other in accordance with another embodiment of the present invention.

According to the present invention and referring now to FIG. 1, a kit 10 for removal of bone 12, for example, a portion of a long bone, from a patient to prepare a bone Cavity 14 for receiving a Joint prosthesis 16 (see FIGS. 11-14), is shown.

The kit 10 includes a guide 20 for cooperation with the long bone 12. The kit 10 also includes a Rotatable tool 22, which is constrained by the guide 20 for removal of the bone 12. The guide 20 includes a first portion 24 of the guide 20, which cooperates with the tool 22. The guide 20 further includes a second portion 26 of the guide 20, which cooperates with the long bone 12.

Preferably, and as shown in FIG. 1, the first portion 24 of the guide 20 defines a channel 30 through the guide 20. The tool 22 is guidable within the channel 30.

Figure 4:
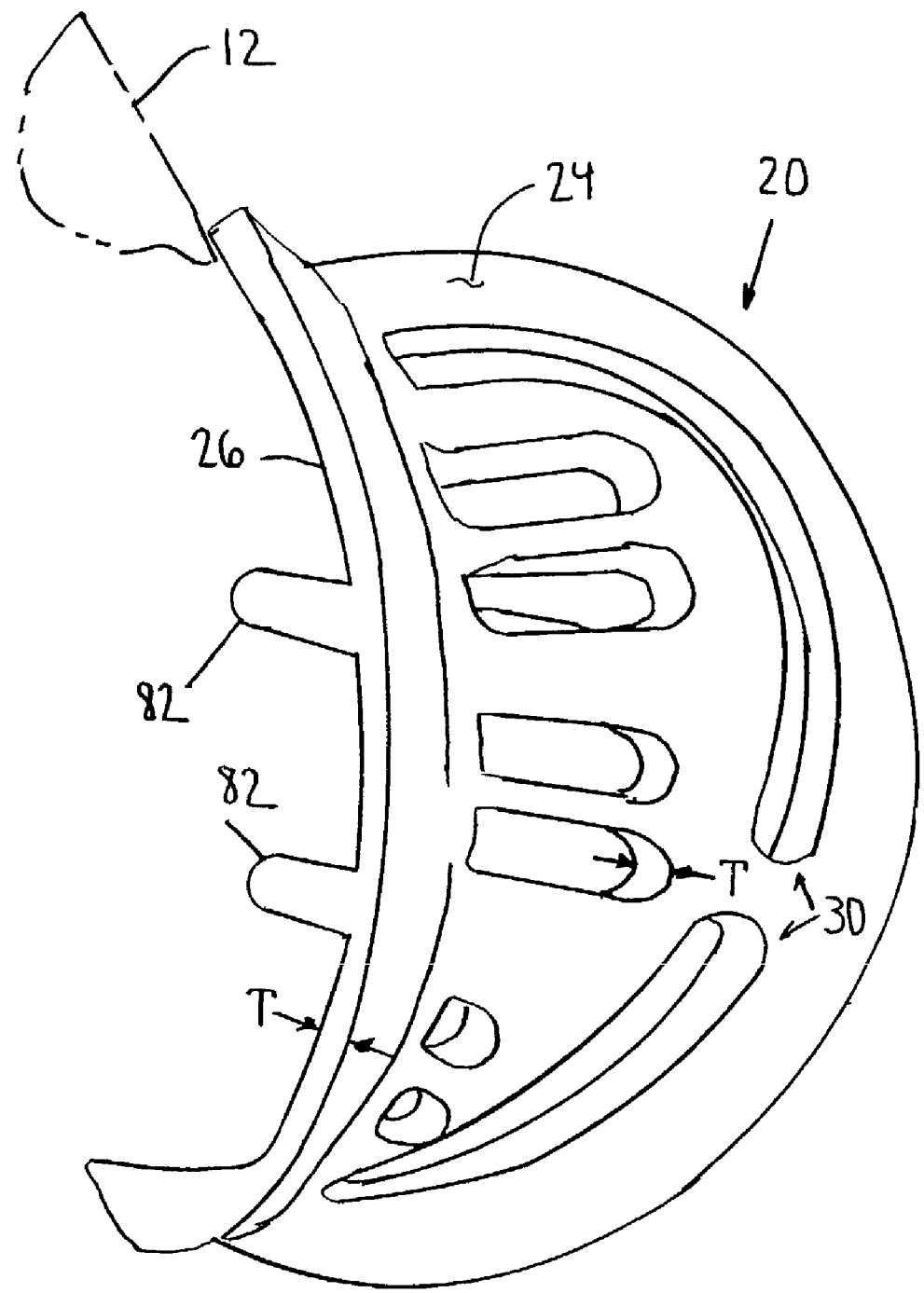
FIG. 4 is a perspective view of a guide according to the present invention in accordance with another embodiment of the present invention.
Figure 5:
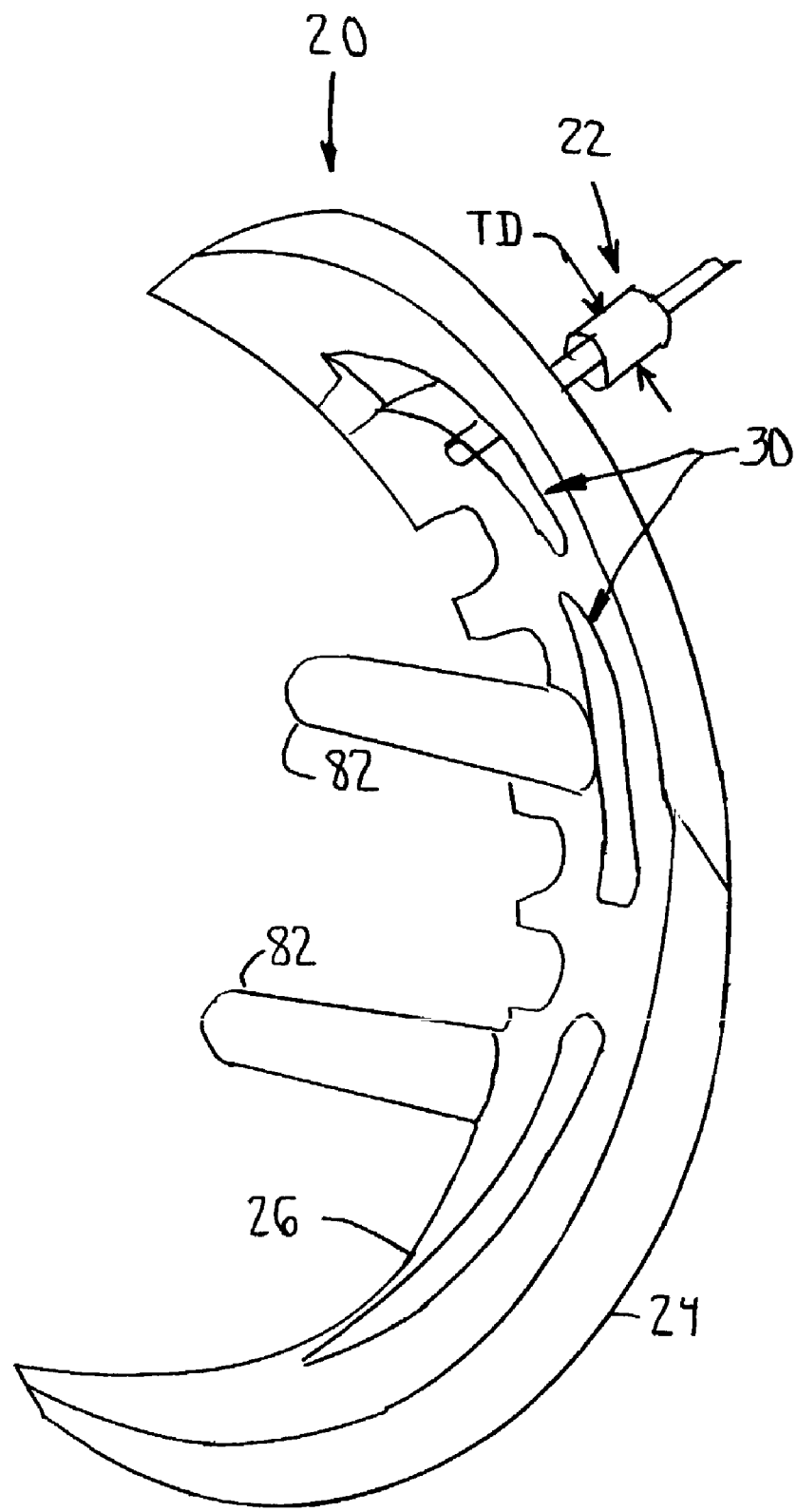
FIG. 5 is a perspective view of the guide of FIG. 1 rotated about 90 degrees from the view of FIG. 4.
Figure 6:
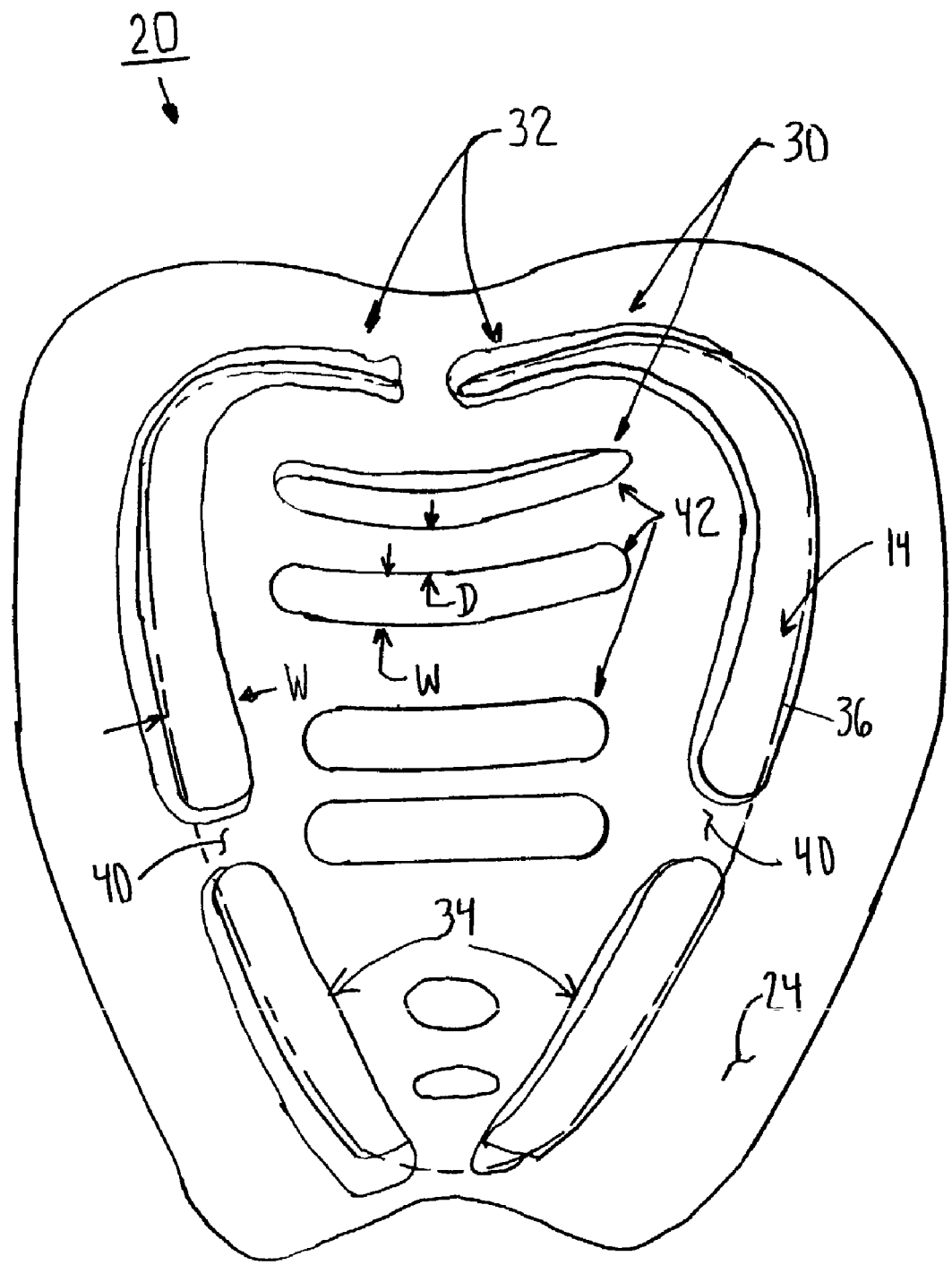
FIG. 6 is plan view of the guide of FIG. 4.

Referring now to FIGS. 4, 5 and 6 the guide 20 is shown in greater detail.

Referring now to FIG. 6, the channels 30 are shown on first portion 24 of the guide 20. As shown in FIG. 6, the channels 30 may include arcuate periphery channels 32 as well as Lower periphery channels 34. The periphery channels 32 and 34 are, as shown in FIG. 6, positioned around periphery 36 of the bone cavity 12 as shown in phantom.

The periphery channels 32 and 34 are utilized to guide the tool 22 in a path, which corresponds, to periphery 36 of the bone cavity 12. To permit structural integrity to the guide 20, the periphery channels 32 must be spaced from each other. The spacing provides for support lands 40 which are positioned between adjacent periphery channels 32 and 34. The lands 40 provide for rigidity to the guide 20. It should be appreciated that upon utilization of the guide 20 and the tool 22, the portions of the bone 12 corresponding to the lands 40 on the guide 20 represent portions of the bone, which must be removed by another tool (for example osteotome not shown).

According to the present invention, in addition to periphery channels 32 and 34, internal channels 42 may be positioned within the guide 20 to provide for removal of additional bone from the bone cavity 12 in an area within the periphery 36 of the bone cavity 12. To provide for sufficient rigidity to the guide 20, the internal channels 42 are separated from each other.

Depending on the thickness of guide 20 and the material chosen for the manufacture of the guide 20, it should be appreciated that the minimal acceptable distance D between adjacent channels may vary. To minimize the amount of material to be removed by the osteotome, the distance D should be the minimum distance required for sufficient strength of the guide 20. For example, for a guide 20 made of a durable material, such as, stainless steel, cobalt chrome or other suitable durable alloy metal having a thickness T, of for example, 0.12 inches, to 0.19 inches and for a guide 20 having channels 30 having a width W of, for example, 0.12 inches and for utilization with ⅛ inch burr tool, the distanced may be as little as 0.04 inches.

Referring again to FIGS. 1, 2 and 3, the guide 20 is shown in position against bone 12. It should be appreciated that the tool, guide and kit of the present invention may be utilized to form a bone cavity in a bone in positions, in addition to the patella femoral joint described in FIGS. 1-6. In fact, the guide and tool of the present invention may be utilized to form any bone cavity, which may be necessary to provide a mounting location for a prosthetic implant.

The guide, tool and kit of the present invention is particularly well suited for utilization in a implant which has a generally uniform thickness and is designed to have an outer contour similar to that of the bone for which it replaces. For example, the tool guide and kit of the present invention may be well suited for unicondylar knee replacement in which a unicondylar knee having a generally uniform thickness is used to replace the resected bone. Other common joints particularly partial implants of the shoulder, knee or hip may be well suited to the use of the guide tool and kit of the present invention.

Referring again to FIGS. 1, 2 and 3, the guide 20 is preferably placed over outer periphery 44 of the bone 12. As shown in FIGS. 1 through 6 the bone 12 is a femur and the guide 20 has an inner periphery 46 on second portion 26 of the guide 20, which preferably conforms, closely to outer periphery 44 of the bone 12.

Figure 2:
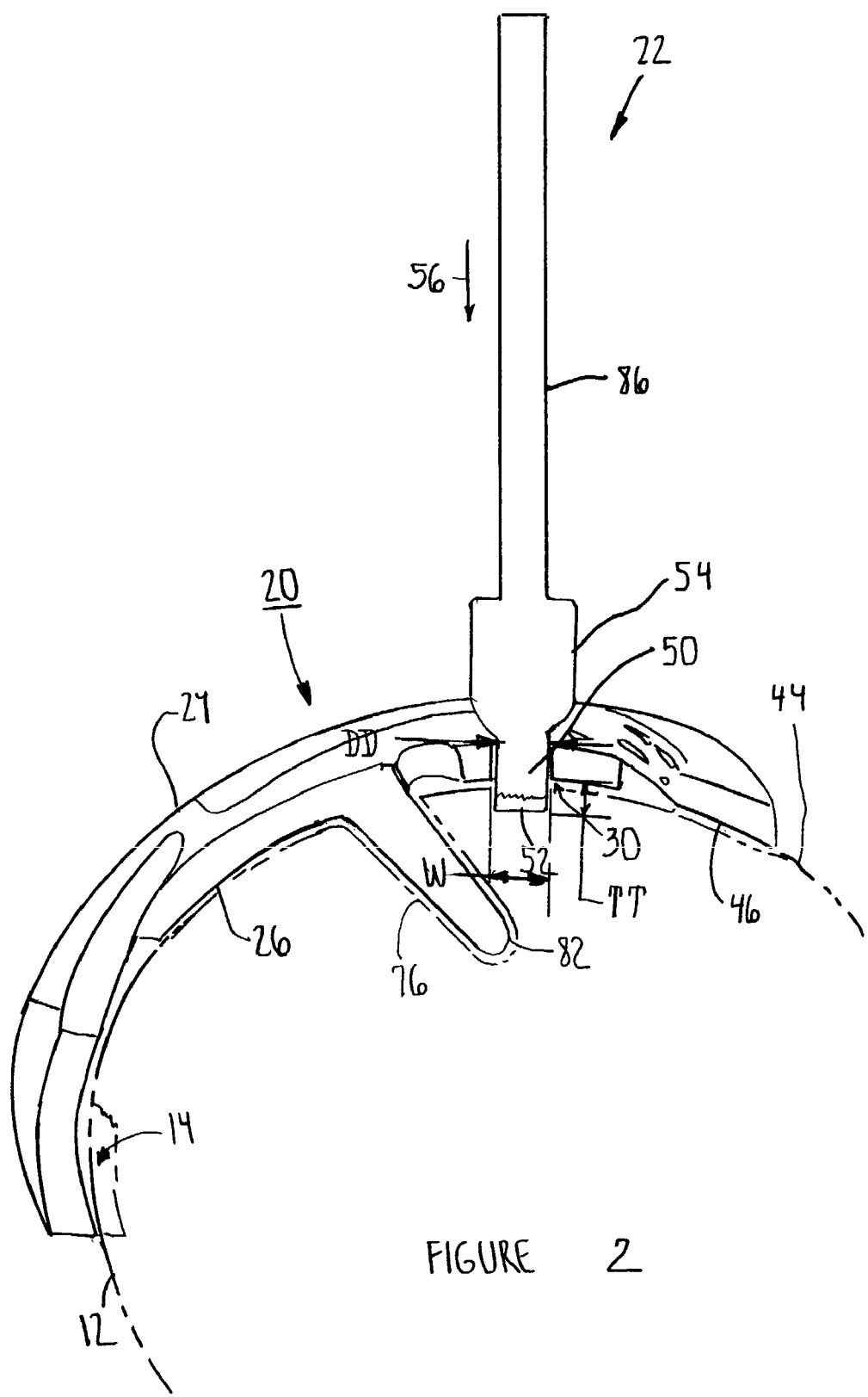
FIG. 2 is a perspective view of the kit of FIG. 1 rotated about 90 degrees from the view of FIG. 4.

Referring now to FIG. 2, the tool 20 includes a body 50 including a cutting edge 52 on an outer periphery thereof. The body 50 has a body diameter DD which is slidingly fitted within the channels 30 of the guide 20. The width W of the channels 30 is thus slightly larger than the diameter DD of the body 50. The tool 22 preferably includes a stop 54, which limits the motion of the tool 22 in the direction of arrow 56 such that the stop 54 rests against the guide 20.

Figure 12:
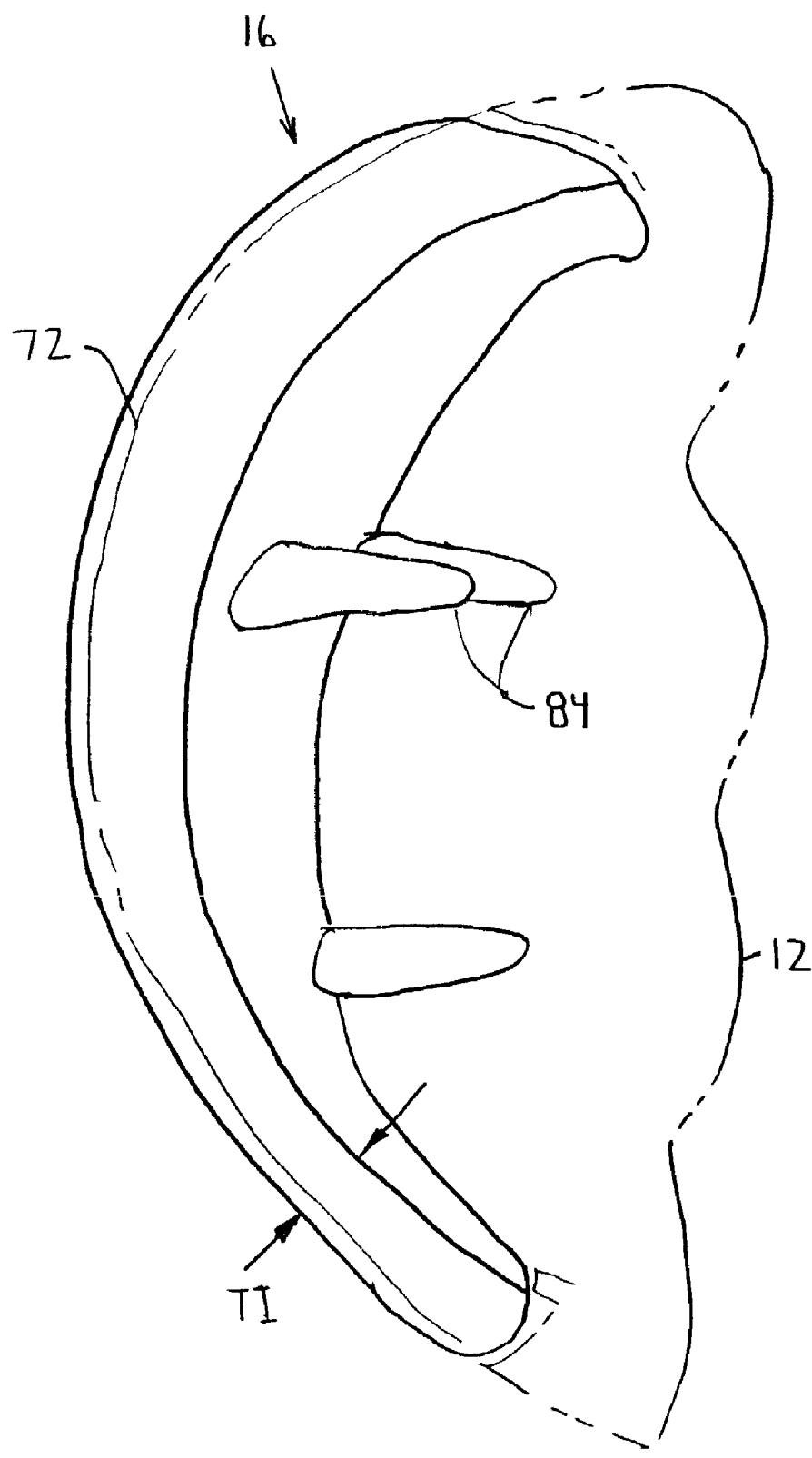
FIG. 12 is perspective view of the prosthesis of FIG. 11.

The cutting edge 52 of the tool 22 extends inwardly from inner periphery 46 of the guide 20 a distance TT approximately equaled to the thickness TI of the implant (see FIG. 12). Since the inner periphery 46 of the guide 20 is shaped to conform to the outer periphery 44 of the bone 12, the extending of the tool 22 a distance TT below the inner periphery of the guide 20 results in the bone cavity 14 to have a thickness or depth approximately equal to TT.

Referring now to FIGS. 11 through 14, implant 16 is shown implanted into bone cavity 12. The implant 16 may be surgically implanted utilizing the tool guide and kit of the present invention. As stated earlier the implant 16 may have any suitable shape and may be an implant to replace any joint of the human anatomy or a portion of such a joint. Joints having a generally uniform thickness are particularly well suited for the present invention. Such joints may include unicondylar knee joints or patella femoral joint which is shown in FIGS. 11 through 14.

Figure 3:
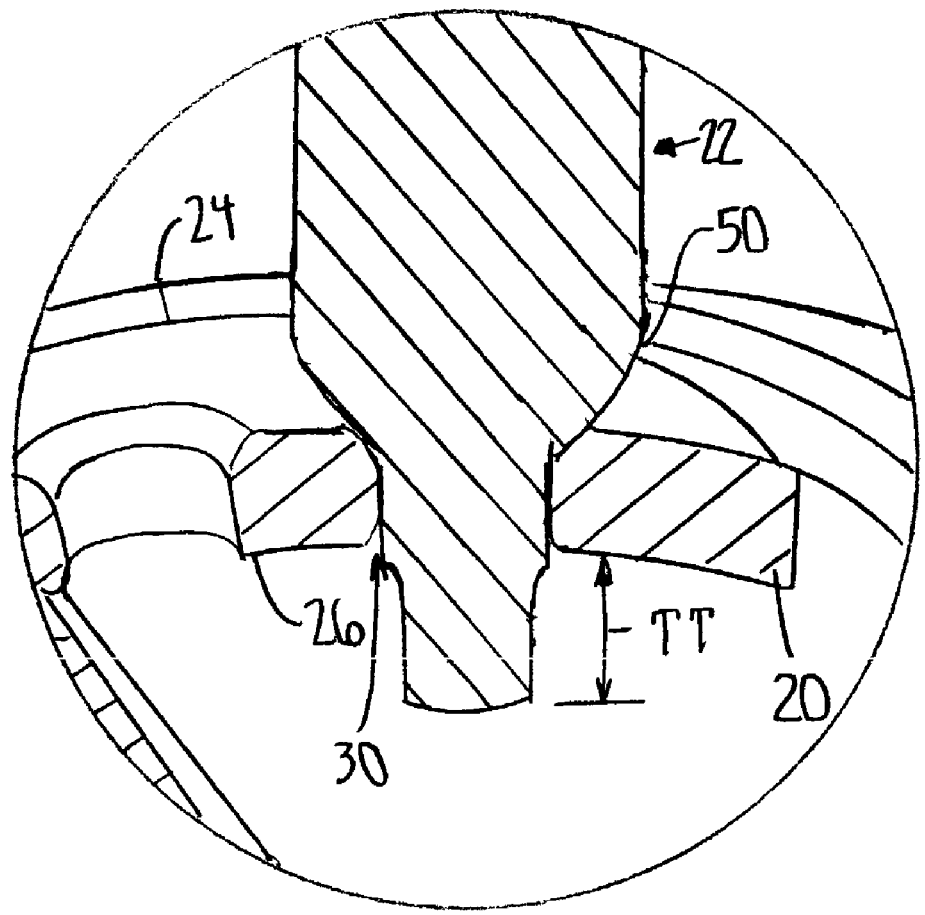
FIG. 3 is an enlarged partial perspective view of the kit of FIG. 2 showing the tool in engagement with the guide in greater detail.
Figure 13:
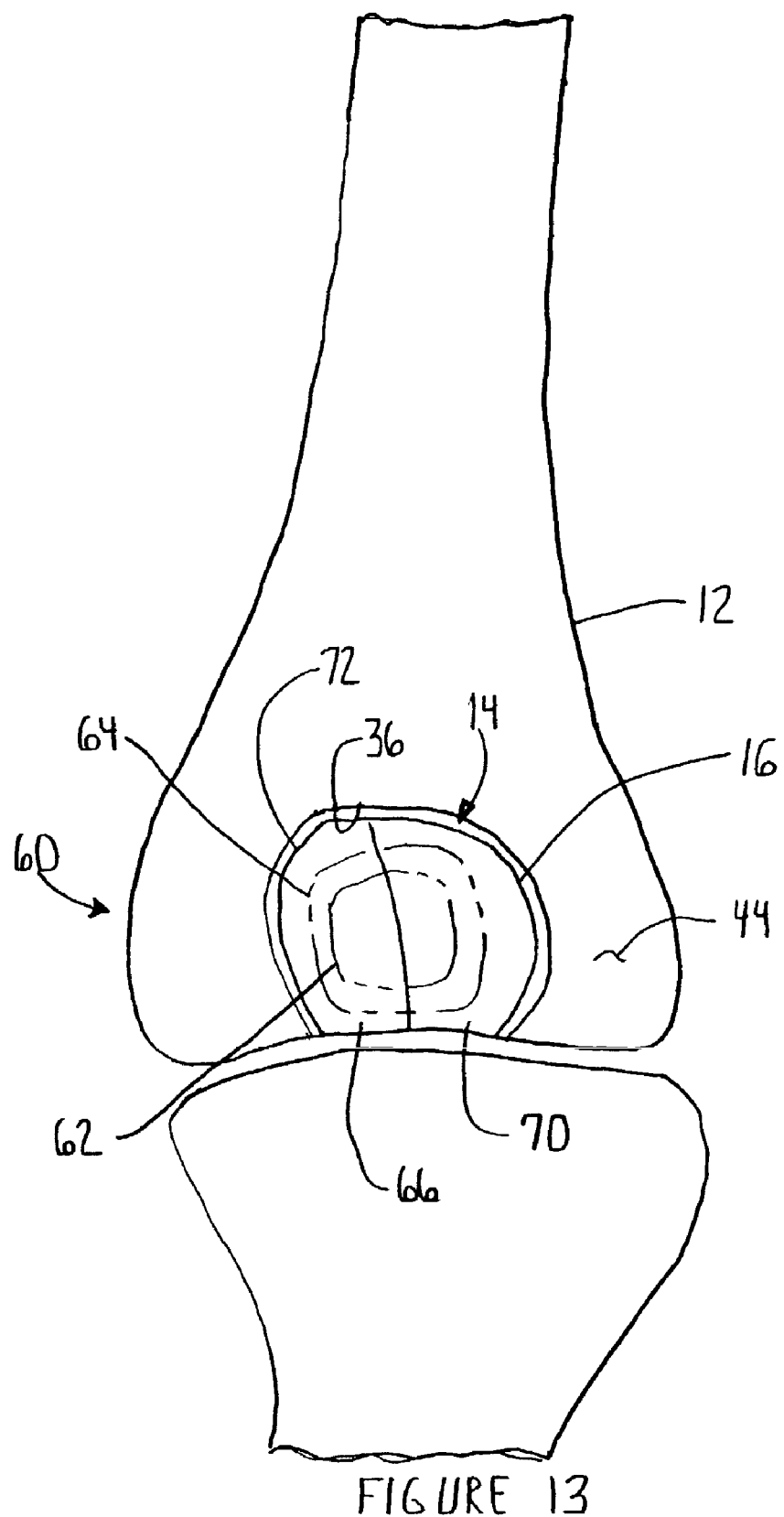
FIG. 13 is a partial plan view of a femur and tibia showing the prosthesis of FIG. 11 placed in the femur with the leg in extension.
Figure 14:
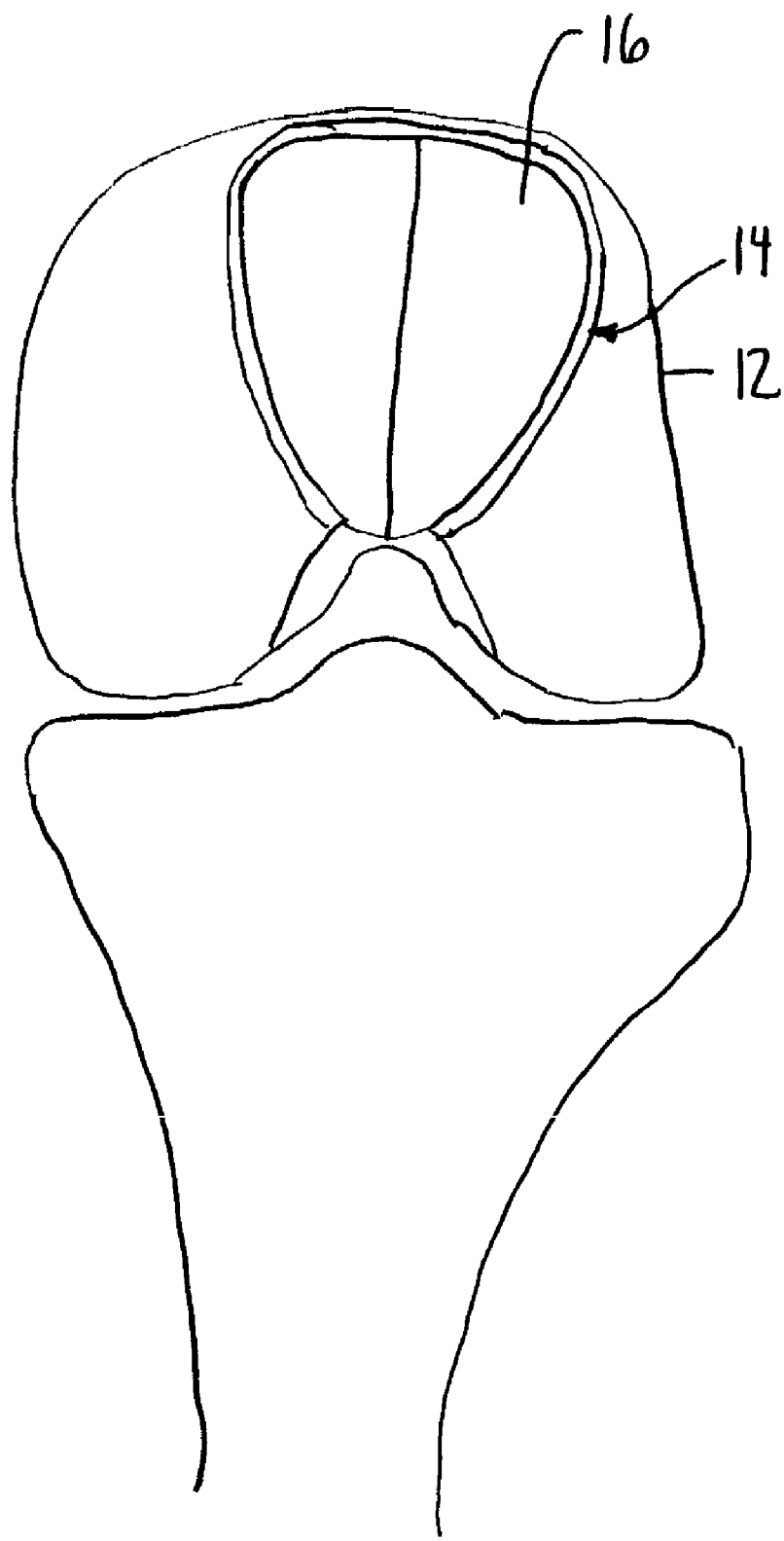
FIG. 14 is a partial plan view of a femur and tibia showing the prosthesis of FIG. 11 placed in the femur with the leg in flexion.

Referring now to FIG. 13 the prosthesis 16 is shown implanted on a left femur 12. The prosthesis 16 as shown in FIG. 3 is a portion of a patella femoral joint 60. The patella femoral joint (PFJ) 60 is used to replace the natural patella when the portion of the knee joint requires a prosthesis due to rheumatoid or osteoarthritis for example. The patella femoral joint 60 may include a patella component 62 as well as a patella bearing 64, which is placed between the patella component 62, and the prosthesis or trochlear component 16.

Due to the unsymmetrical nature of the anatomical femur 12, the trochlear component 16 of the patella femoral joint 60 is likewise asymmetrical including a smaller medial portion 66, as well as a larger lateral portion 70. The PFJ trochlear component 16 defines an outer periphery 72 thereof. The trochlear implant periphery 72, as shown in FIG. 13, is slightly smaller than periphery 36 of the bone cavity 14. It should be appreciated that the trochlear prosthesis for the right knee is similar and complimentary to the left knee trochlear prosthesis 60 as shown in FIG. 13.

The proper position of the trochlear prosthesis 60 with regard to the femur 12 may be determined either by surgeon skill, by templating relative to anterior/posterior and medial/lateral x-ray techniques or by computer or other high technology positioning techniques. When the proper position of the PFJ trochlear component 16, with regard to the femur 12 is determined, the guide 20 must be properly secured in position on the femur 12.

Figure 15:
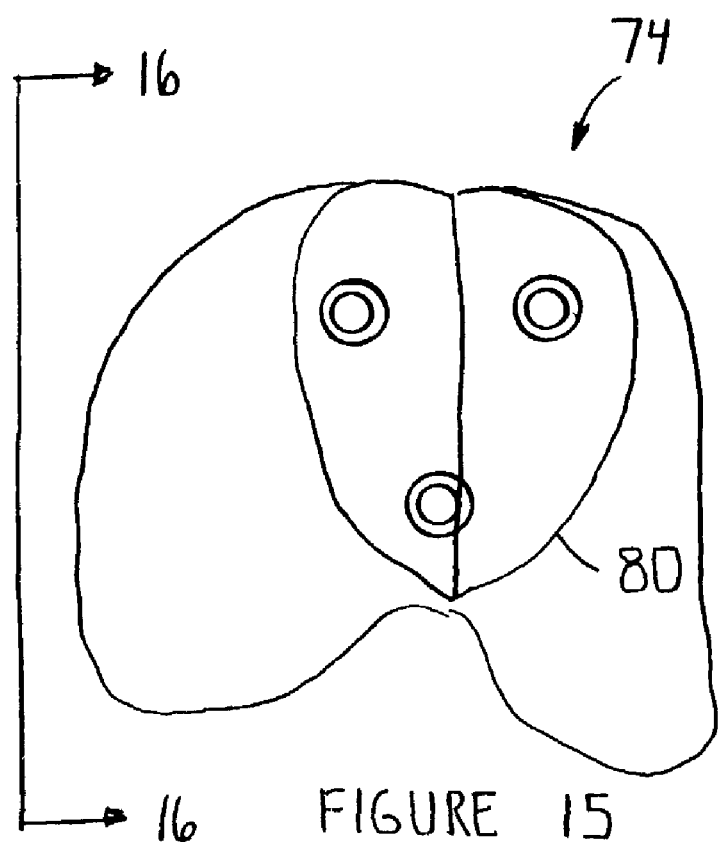
FIG. 15 is a partial plan view of a drill guide installed on a femur for preparing the femur with holes for cooperation with the guide of FIGS. 1 and 2.
Figure 16:
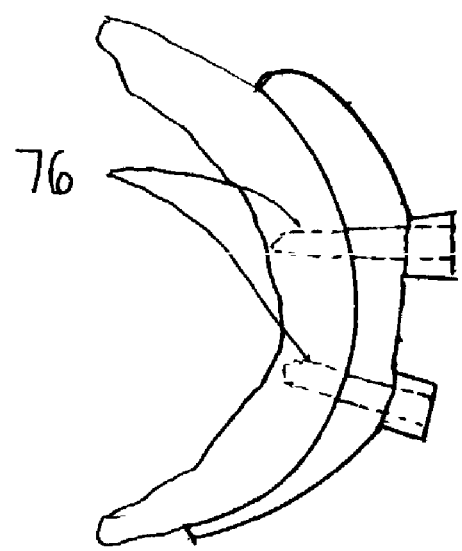
FIG. 16 is a partial plan view of the drill guide of FIG. 15 along the lines 16-16 in the direction of the arrows.

When utilizing the guide 20 of FIGS. 1 through 6 a trochlear component drilling guide 74 as shown in FIGS. 15 and 16 may be utilized. The drilling guide 74 of FIGS. 15 and 16 has been utilized in higher art implanting techniques. The drilling guide 74, when used in prior art implanting techniques, is utilized by first visually positioning the drilling guide 74 in a predetermined appropriate position.

Techniques utilized to position this drilling guide may include, among other things, surgeon expertise and x-ray templating. The drilling guide 74 is positioned in its proper place against femur 12 and held in position while a drill is utilized to form anchor peg holes 76 in the femur 12. When utilizing prior art techniques for the drilling guide 74, a scribe or edge is formed around outer periphery 80 of the drilling guide 74 so that the scribed portion of the femur may be resected by prior art techniques utilizing for example osteotomes.

Referring now to FIGS. 1 through 6, to properly orient the guide 20 with respect to the femur 12, the guide 20 may include a first orientation feature for cooperation with an orientation feature on the prosthesis. For example, and referring to FIG. 2, the orientation feature on the prosthesis may be in the form of a peg 82 extending inwardly from inner periphery 46 of the guide 20. The first orientation feature or guide peg 82 of the guide cooperates with an orientation feature on the bone 12 in the form of, for example, one of the anchor peg holes 76. Preferably, the guide peg 82 closely conforms to the anchor peg 76 for an accurate, precise, and snug fit of the guide to the bone 12.

While a solitary peg 82 may be sufficient to orient the guide 20 against the bone 12, preferably, and referring to FIG. 4, a pair of guide pegs 82, which are spaced apart from each other are utilized in the guide 20. While the prosthesis 16 of FIG. 4 includes two spaced apart anchor pegs 84, it would be appreciated that additional guide pegs 82 may be utilized to secure the guide 20 of FIG. 2.

Referring again to FIG. 2, the rotatable tool 22 is shown according to the present invention. The rotatable tool 22 is adapted for removal of bone 12 from a patient to prepare the bone cavity 14 for receiving joint prosthesis 16. The tool 22 is constrainable by the guide 20 for removal of the bone 12.

As shown in FIG. 2 the rotatable tool may be in the form of a rotating burr tool. The tool 22 may include the body 50, which includes cutting edge 52 formed on a periphery thereof. A stem 86 is operably associated with the body 50. The stop 54 is positioned between the body 50 and the stem 86 for cooperation with the guide 20 to limit the movement of the tool 22 in the direction of the arrow 56.

Referring now to FIGS. 7 through 10 the bone cavity 14 prepared utilizing the tool guide kit and method of the present invention is shown on a left femur.

Figure 7:
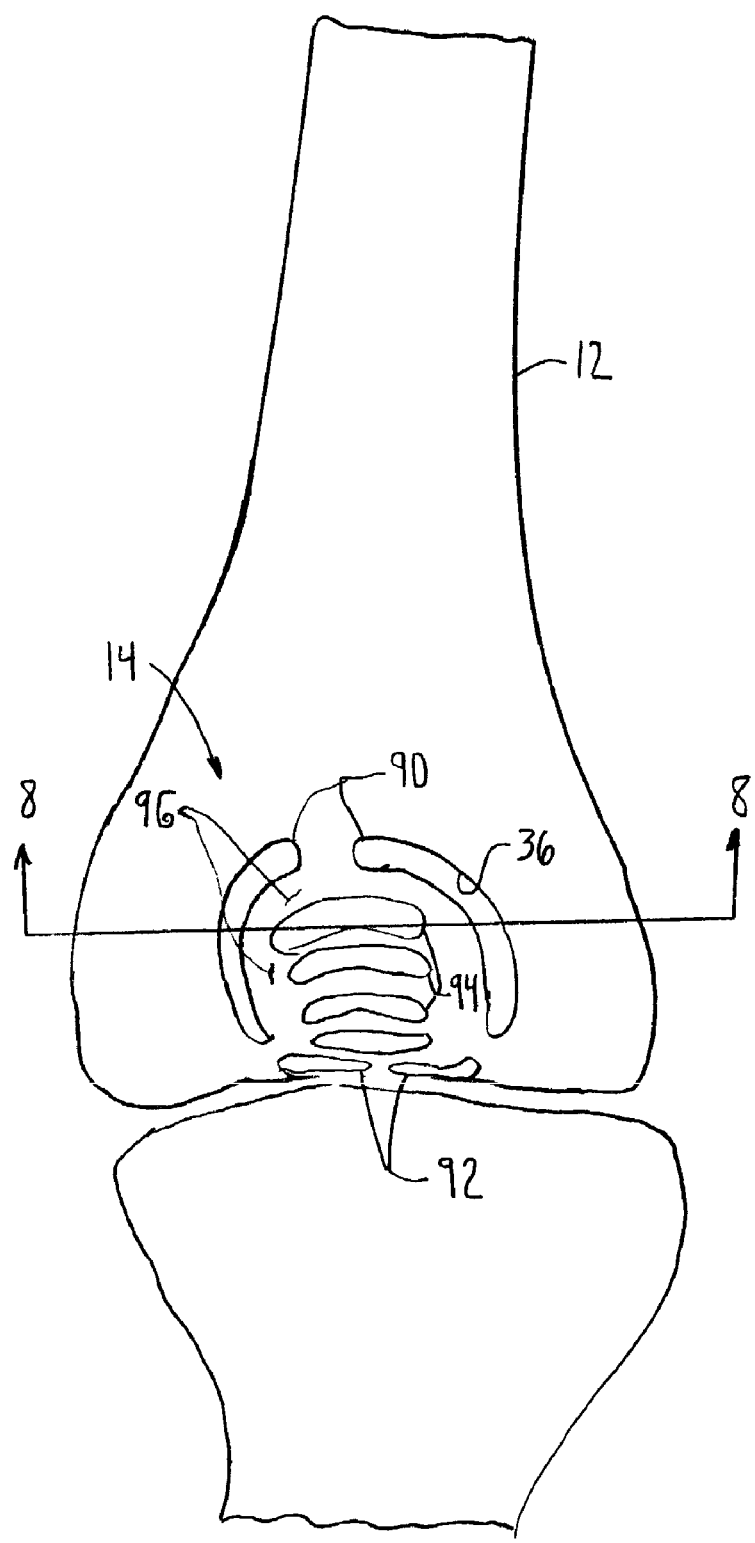
FIG. 7 is a partial plan view of a femur and tibia showing the cuts placed in the femur by the kit of FIGS. 4-6 in accordance with an embodiment of the present invention.

Referring now to FIG. 7, partially formed or completed cavity 14 is shown on the femur 12. The partially completed cavity 14 includes medial and lateral arcuate periphery grooves 90 which correspond to the arcuate periphery channels 32 of the guide 20. The partially completed cavity 14 further includes lower periphery grooves 92 corresponding to the lower periphery channels 34 of the guide 20. Further, the cavity 14 may include internal grooves 94 which correspond to the internal channels 42 of the guide 20. Located between the grooves 90, 92 and 94 are lands 96 corresponding to lands 40 of the guide 20.

Figure 8:
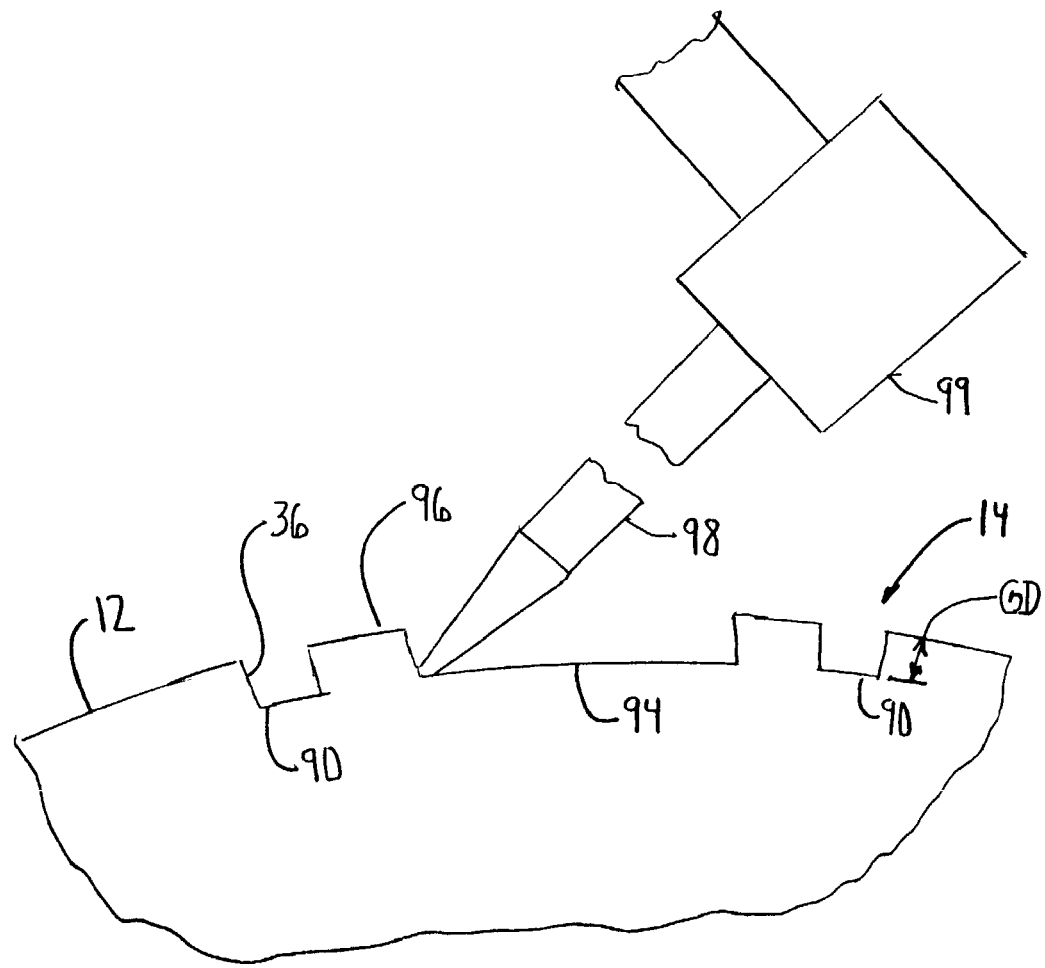
FIG. 8 is a partial cross section view of the femur of FIG. 1 along the lines 8-8 in the direction of the arrows showing the use of an osteotome to remove bone.

Referring now to FIG. 8, a second tool in the form of a chisel like device called an osteotome 98 is shown in use to remove the lands 96 from the femur 12. A striking device in the form of a hammer 99 may be utilized to remove bone with the osteotome 98. In operation, the osteotome is positioned in one of the grooves, for example, groove 94 and the hammer 98 is struck against the osteotome 98 to remove for example, the land 96 between the peripheral grove 90 and the internal groove 94.

Figure 9:
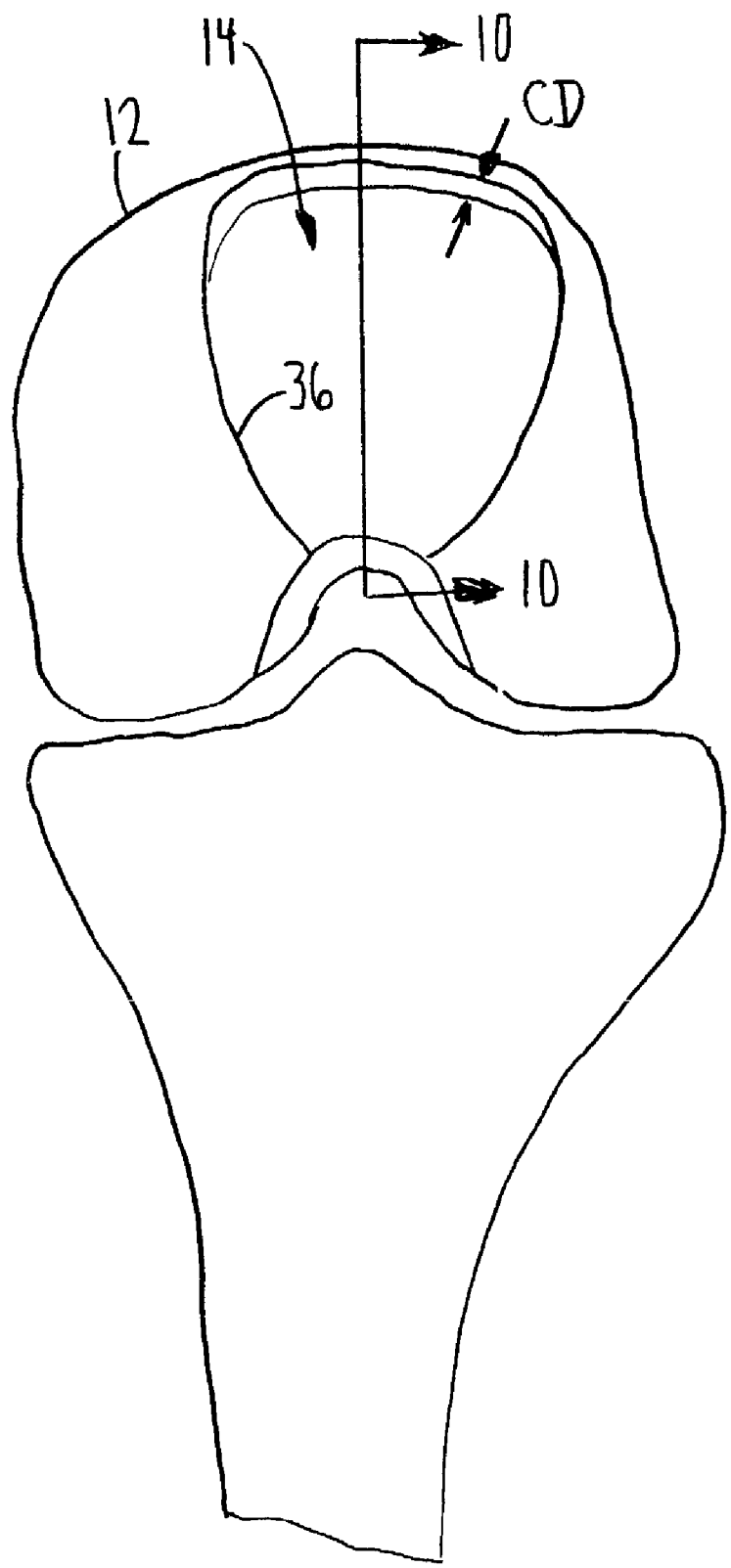
FIG. 9 is a partial plan view of a femur and tibia showing a bone cavity for receiving a joint prosthesis placed in the femur in accordance with an embodiment of the present invention.

Referring now to FIG. 9, the femur is shown with the cavity 14 having been completed, and the lands 96 between the grooves 90, 92 and 94 (See FIG. 7) having been removed. The cavity 14 has the outer periphery 36 into which the prosthesis 16 may be fitted. The cavity 14 also has a cavity depth CD which is approximately equal to the groove depth GD (see FIG. 8) formed by the tool when making the grooves 90, 92 and 94 in the femur 12. It should be appreciated that the groove depth GD is approximately equal to the depth TT of the tool 22 in the guide 20 as shown in FIG. 2.

Figure 10:
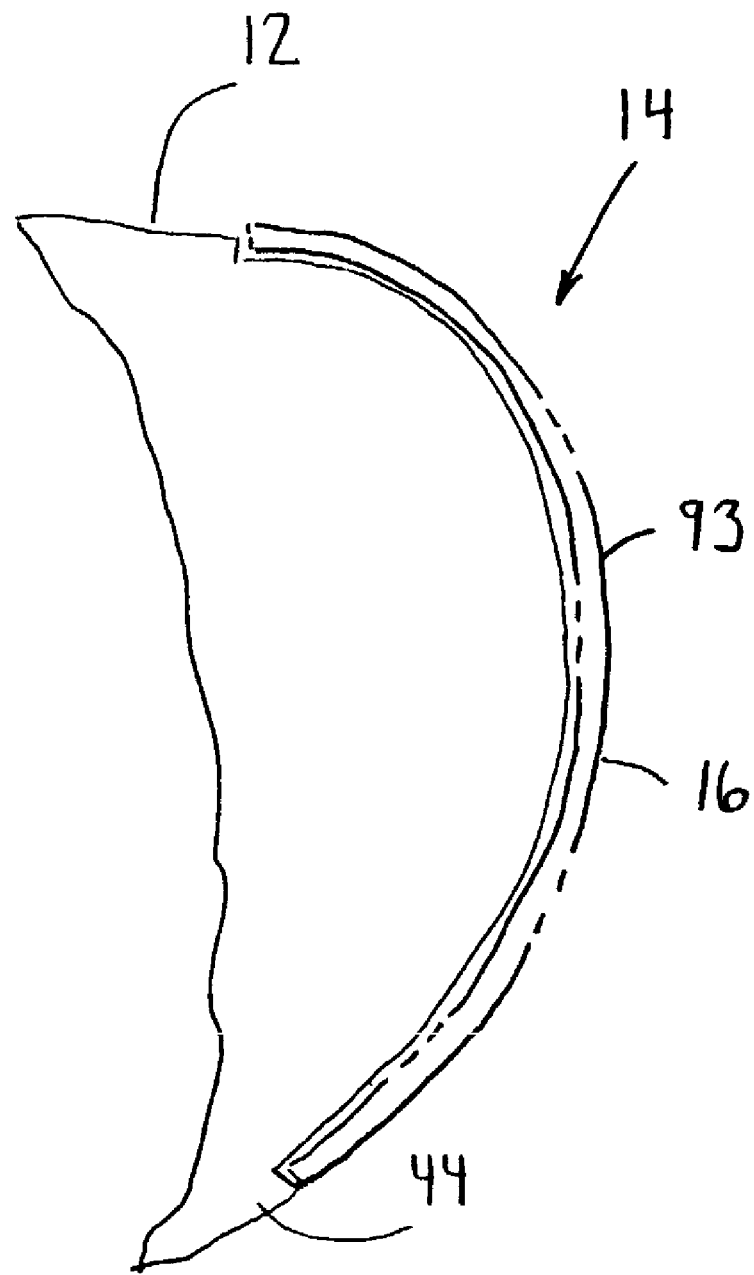
FIG. 10 is a cross section view of the guide of FIG. 1 along the lines 10-10 in the direction of the arrows.

Referring now to FIG. 10 the cavity 14 is shown in cross section in the femur 12. The prosthesis 16 is shown in phantom within the cavity 14. It should be appreciated that the surface 93 of the prosthesis 16 is in general alignment with outer periphery 44 of the femur 12.

Figure 17:
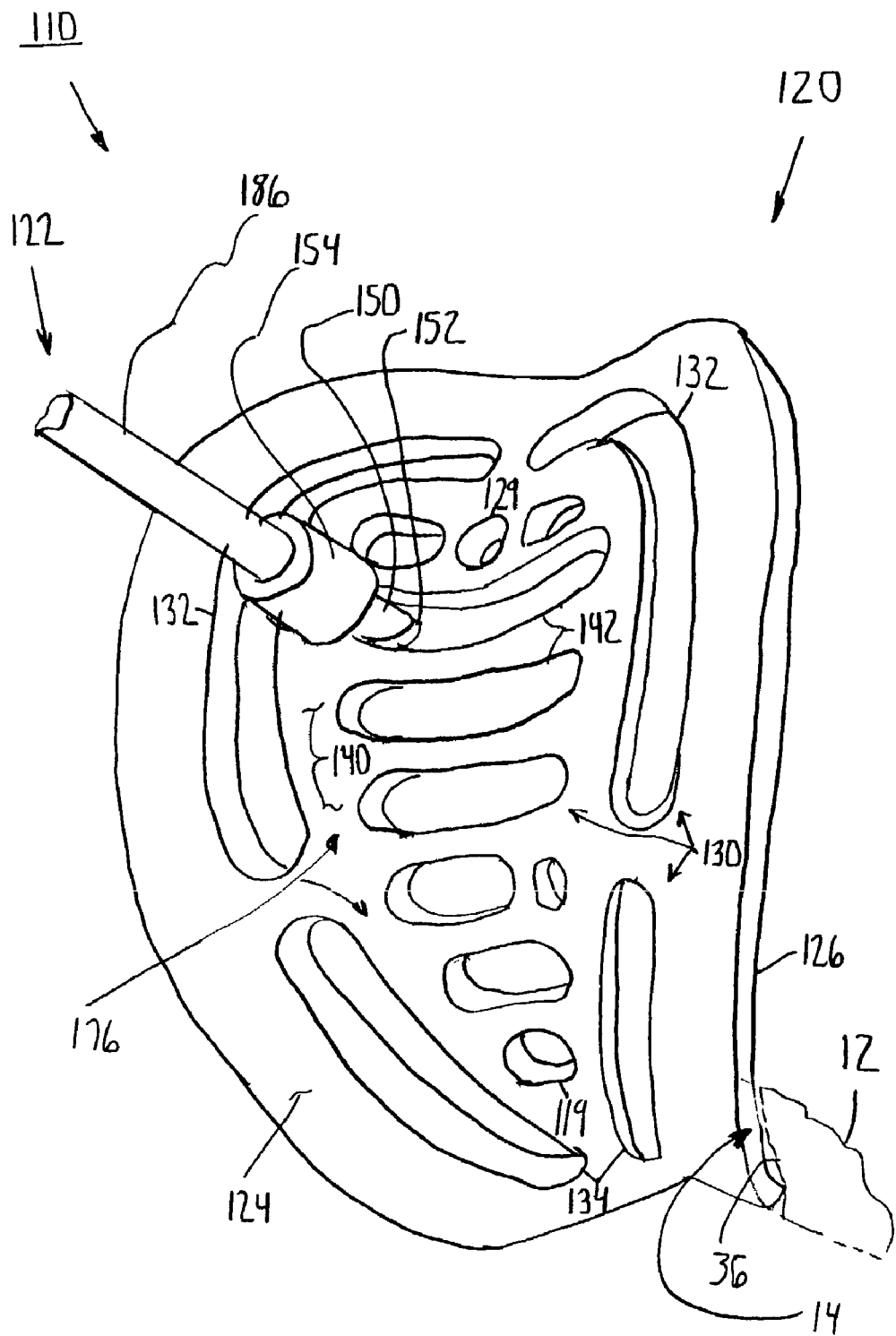
FIG. 17 is a perspective view of a kit according to the present invention including a guide and tool shown in cooperation with each other in accordance with another embodiment of the present invention.
Figure 18:
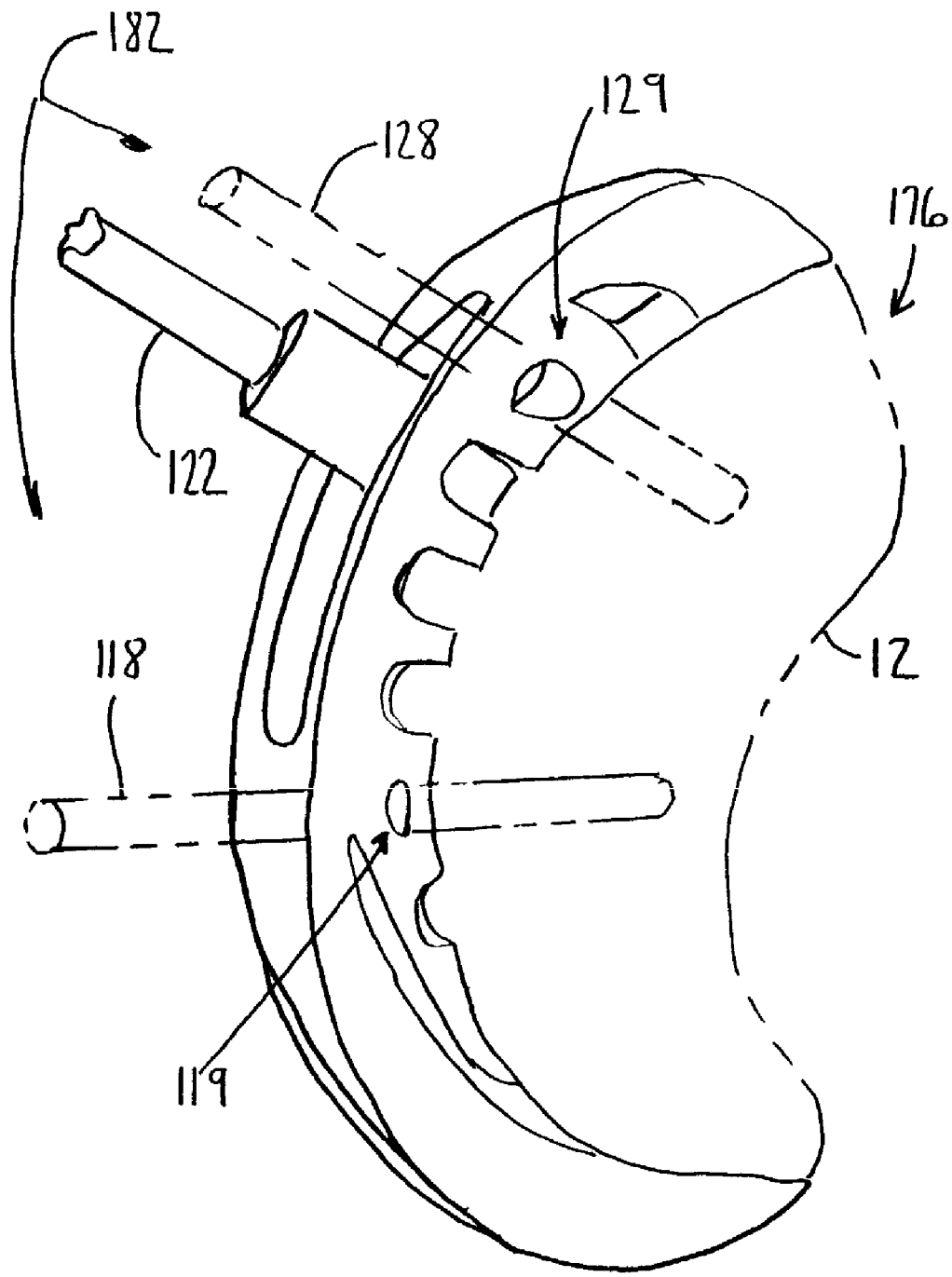
FIG. 18 is a perspective view of the kit of FIG. 15 rotated about 90 degrees from the view of FIG. 15.

Referring now to FIGS. 17 and 18 another embodiment of the present indention is shown as kit 110. The kit 110 includes a guide 120, which cooperates with a tool 122. The tool 122 is similar to tool 22 of FIGS. 1 through 6 and includes a stem 186 to which stop 154 is attached. Extending from the stop 154 is a body 150. At the end of body 150 is a cutting edge 152 for removing bone 12. The tool 122 may be substantially similar to the tool 22 of FIGS. 1 through 6 and be made of any suitable, durable material for example a tool steel.

The guide 120 is similar to guide 20 of FIGS. 1 through 6 except that guide 120 includes guide openings 176 and do not include guide pegs 82 as in the guide 20 of FIGS. 1 through 6. The kit 110 of FIGS. 17 and 18 further include guide pins 182 which cooperate with the guide openings 176 of the guide 120 (see FIG. 18).

When utilizing the guide 120 of FIGS. 17 and 18, the guide 120, like the drilling guide 74 of FIGS. 15 and 16, is positioned utilizing any suitable surgical technique including, for example, a visual alignment of the guide 120 onto the femur or through the utilization of templates, for example, x-ray templates, a computer technique, or any other alignment technique. Once the guide 120 is placed in the proper position on the femur, the guide pins 182 are placed in position through the guide openings 176 in the guide 120. The guide pins 182 may be in the form of self drilling pins or connectors and a power tool (not shown) is utilized to secure the connectors or self drilling pins 118 and 128 into the femur 12. The guide 120 is thereby secured in position in the femur 12.

By utilizing the guide apparatus 176 and the guide pins 182 the anchor peg holes 76 are left in a unused or unworn condition so that the drilling guide 74 may be installed into the bone cavity 14 after the bone cavity 14 is prepared such that the anchor peg hole 76 remain in pristine condition for an accurate and secure installation of the prosthesis 16.

Channels 130 are preferably positioned in the guide 120, and the channels 130 include upper arcuate periphery channels 132 and lower periphery channels 134 which, when utilized with the tool 120, may cause the tool 122 to form periphery 36 of the cavity 14. The channels 130 preferably also include internal channels 142, similar to channels 42 of the guide 20 of FIGS. 1 through 6. The upper arcuate periphery channels 132 and the lower periphery channels 134 are similar to the upper arcuate channels 32 and the lower periphery channels 34 of the guide 20 of FIGS. 1 through 6.

Figure 19:
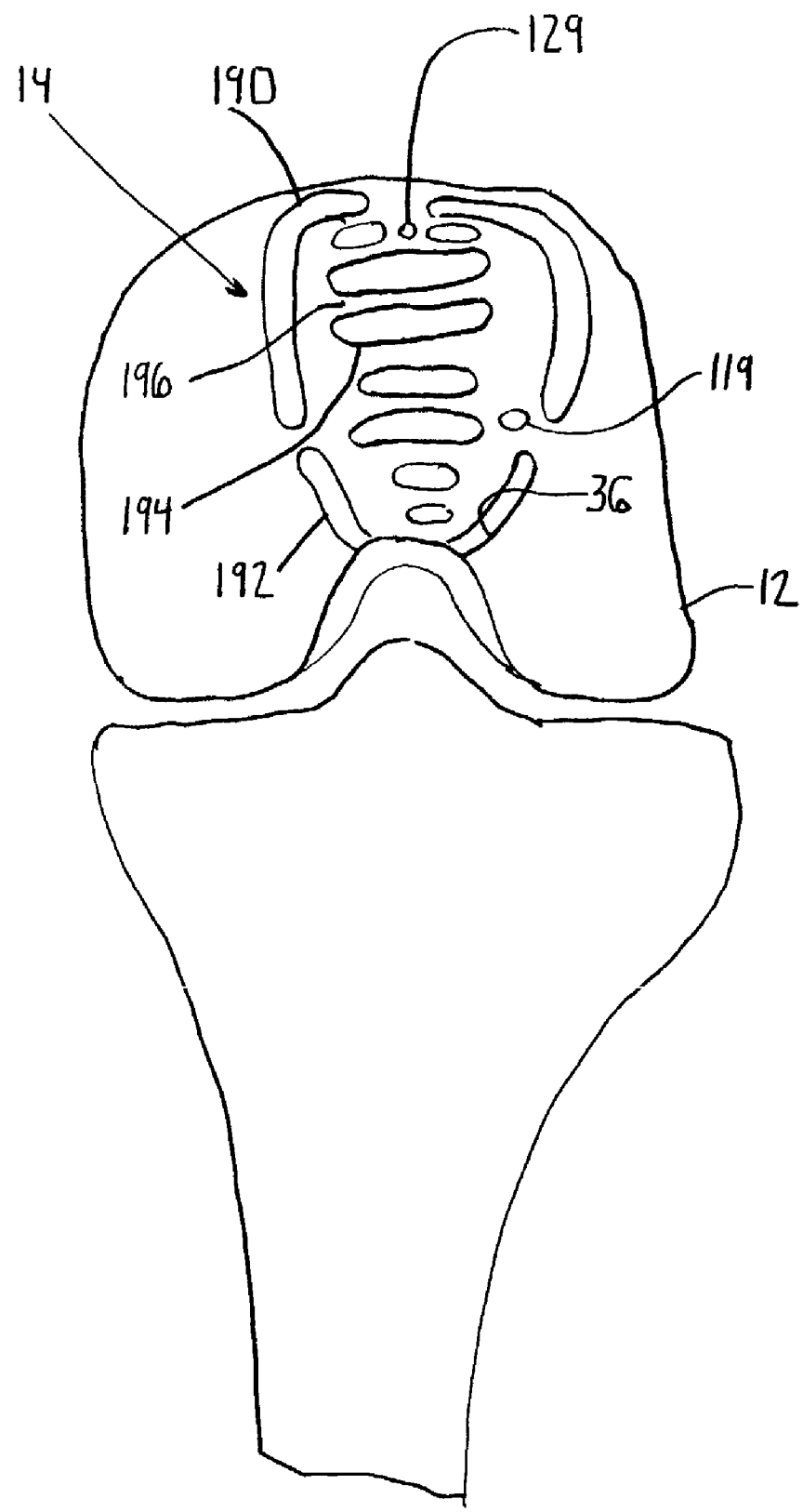
FIG. 19 is a partial plan view of a femur and tibia showing the cuts placed in the femur by the kit of FIGS. 15 and 16.

Referring now to FIG. 19, a femur 12 is shown having a partially formed bone cavity 14 formed on the femur 12 utilizing the guide 120 of FIGS. 17 and 18. The cavity 14 includes arcuate periphery grooves 190 and lower periphery grooves 192, which correspond to the upper arcuate channels 132 and lower arcuate channels 134. The cavity 14 also includes internal grooves 194 which correspond to internal channels 142 in the guide 120. Lands 196 in the cavity 14 correspond to lands 140 on the guide 120 of FIGS. 17 and 18. Similar to the cavity 14 formed by the guide 20 of FIGS. 1 through 6, the lands 196 are similarly removed by an osteotome and hammer (not shown).

Figure 21:
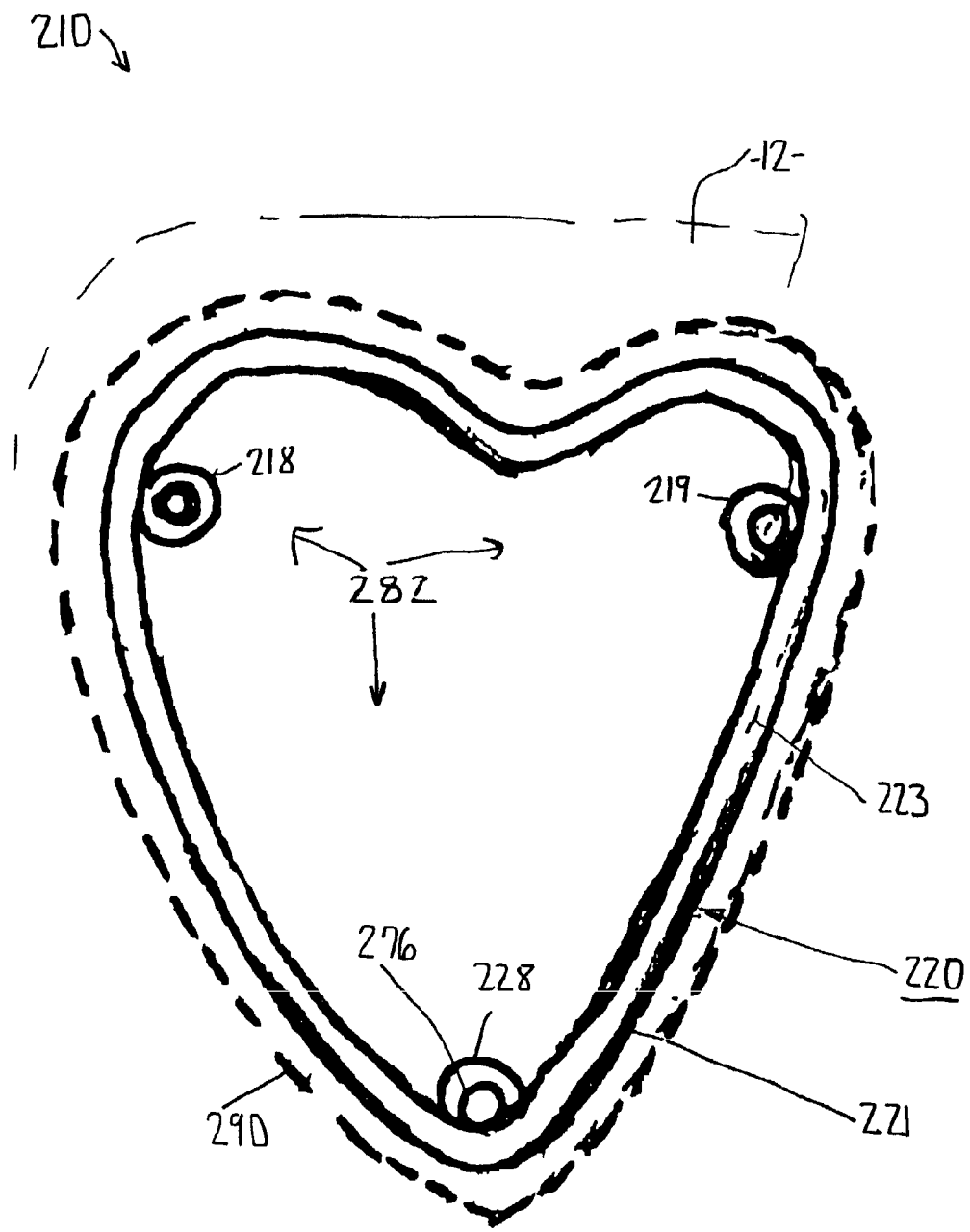
FIG. 21 is a plan view of a peripheral cutting tool guide in accordance to yet another embodiment of the present invention.
Figure 21B:
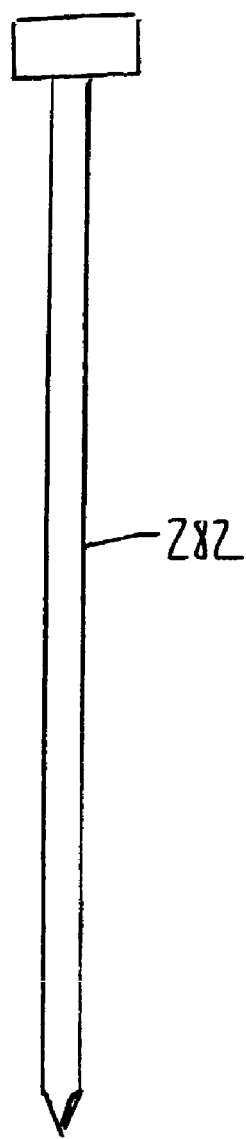
FIG. 21B; is a plan view of a pin for cooperation with the cutting tool guide of FIG. 21.
Figure 21A:
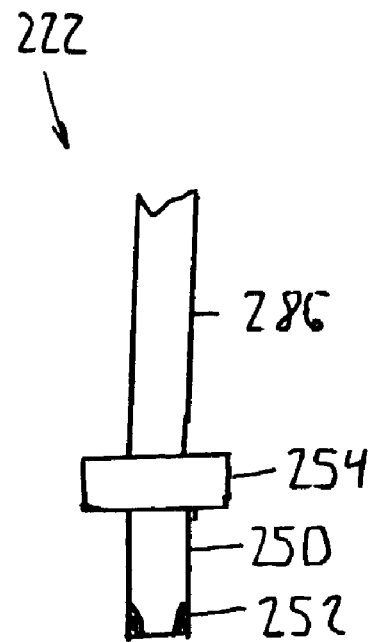
FIG. 21A; is a plan view of a cutting tool for cooperation with the cutting tool guide of FIG. 21.
Figure 22:
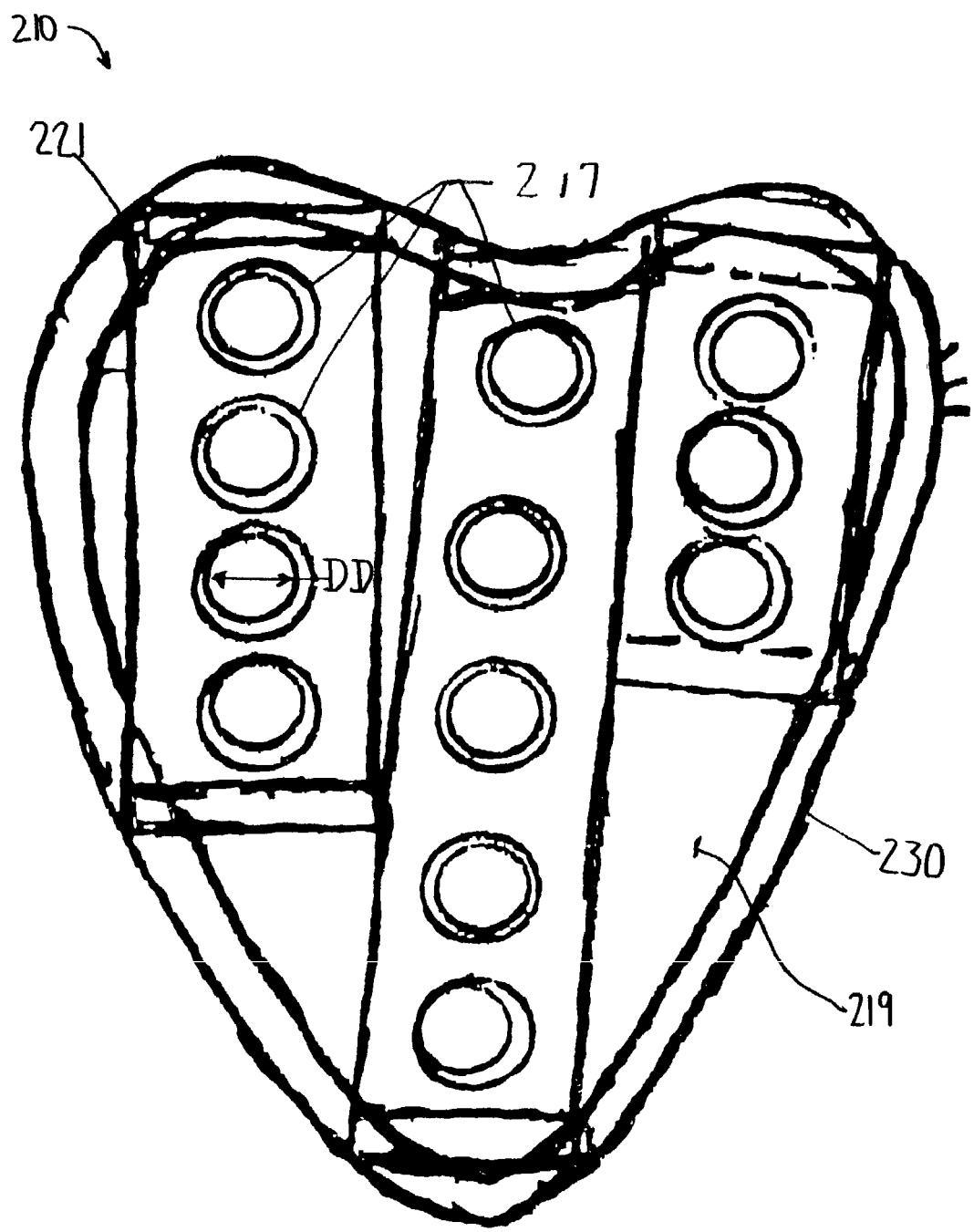
FIG. 22 is a plan view of a drill guide to be used with the periphery cutting tool guide of FIG. 21.
Figure 22:
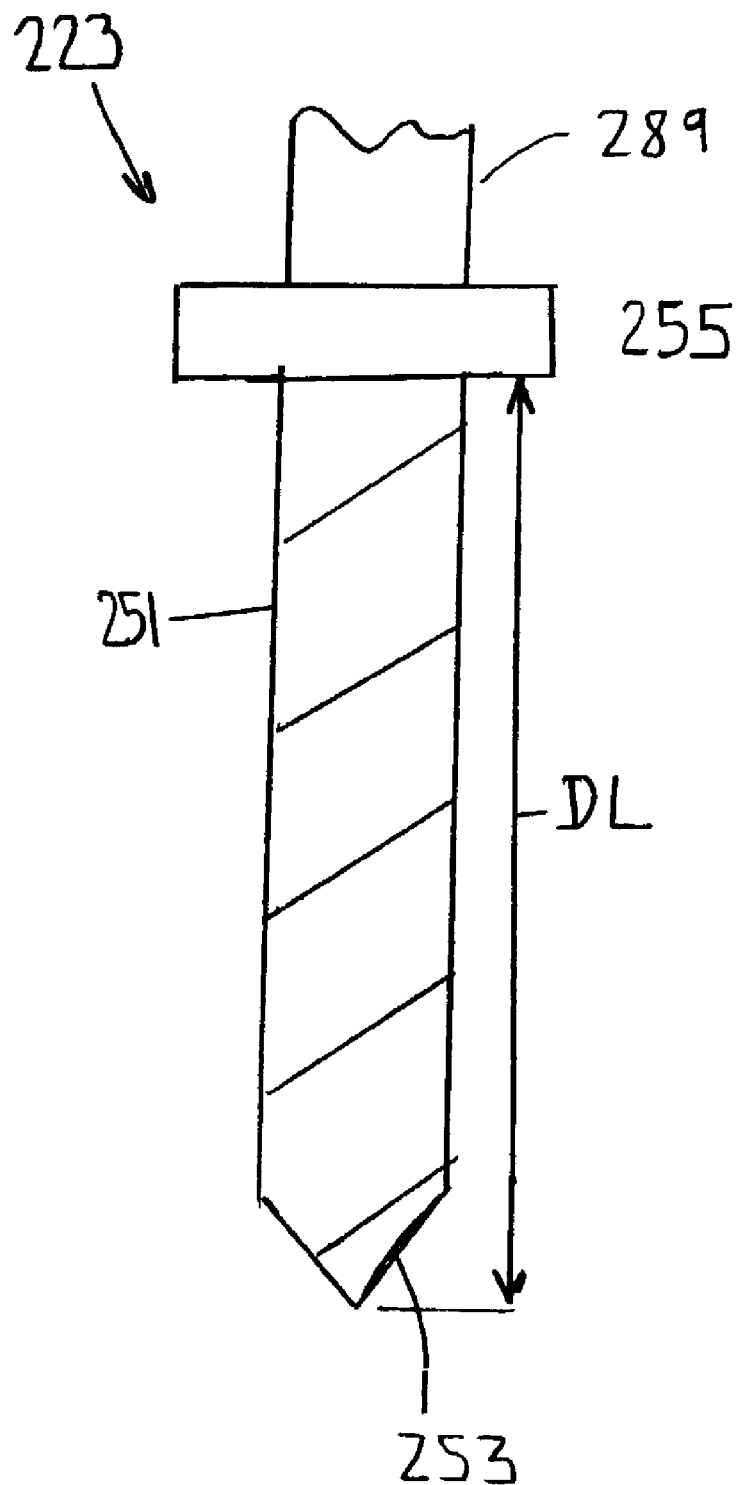
Figure 23:
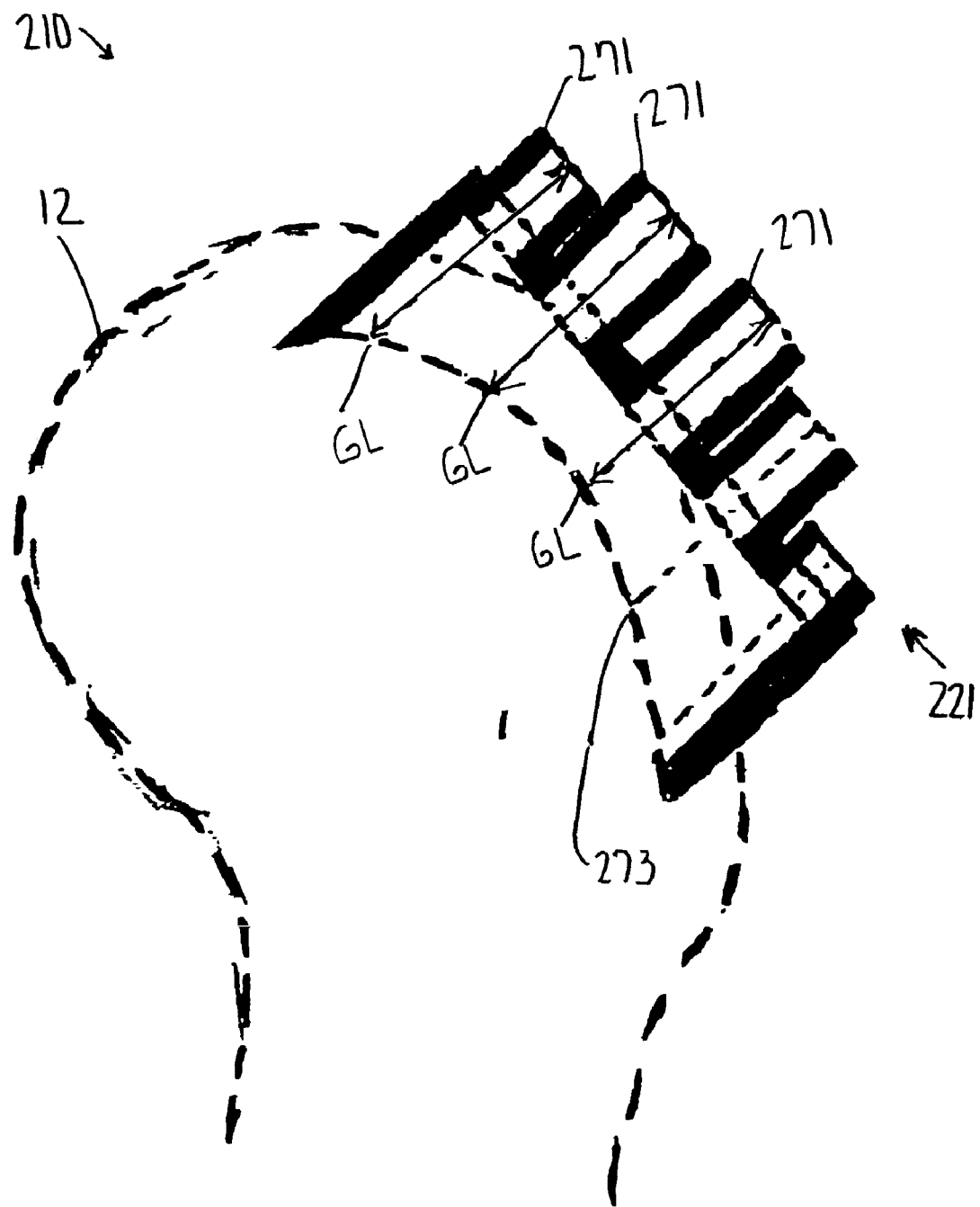
FIG. 23 is a cross sectional view of the drill guide of FIG. 22 along the lines 23-23 in the direction of the arrows.

Referring now to FIGS. 21 through 23, a further embodiment of the present invention is shown as kit 210. The kit 210 includes a cutting tool guide 220 which cooperates with a cutting tool 222. The cutting tool 222 is similar tool 22 of FIGS. 1-6 and may include a stem 286 254, is a body 250. At the end of the body 250 is a cutting edge 252 for removing bone. The tool 222 may be substantially similar to the tool 22 of FIGS. 1-6 and be made of any suitable, durable material, for example a tool steel.

The cutting tool guide 220 is similar to guide 20 of FIGS. 1-6 except that cutting tool guide 220 includes guide openings 276 and does not include guide pegs 82 as in the guide of FIGS. 1-6. The kit 210 of FIGS. 21-23 further includes a guide pin 282 which cooperates with the guide opening 276 of the guide 220.

When utilizing the cutting tool guide 220 of FIG. 21, the guide 220, like the drilling guide 74 of FIGS. 15 and 16, is positioned utilizing any suitable surgical technique including, for example, a visional alignment of the guide 220 onto the femur or the utilization of templates, for example, x-ray templates, a computer technique, or any other alignment technique. Once the guide 220 is placed in the proper position on the femur, one or more guide pins 282 are placed in position through the guide openings 276 in the cutting tool guide 220. The guide pins 282 may be in the form of self drilling pins or connectors and a power tool (not shown) is utilized to secure the connectors or self drilling pins 218, 219 and 228 into the femur 12. The cutting tool guide 220 is thereby secured in position into the femur.

The cutting tool guide 220 includes an outer periphery 221 thereof as well as an upper surface 223. The stop 254 of the tool 222 is brought to rest against the upper surface 223 of the cutting tool guide 220 and limits the depth of the cut on the femur. The body 250 of the tool 222 is guided along outer periphery 221 of the cutting tool guide 220 and is used to form outer periphery groove 290 in the femur 12.

Referring now to FIG. 22, the kit 210 further includes a drill guide 221 which cooperates with drill 223. The drill 223 is similar 222 of FIGS. 1-6 and includes a stem 289 to which stop 255 is attached. Extending from the stop 255 is a body 251. At the end of the body 251 is a cutting edge 253 for removal bone 12. The drill 223 may be substantially similar to the tool 222 of FIGS. 1-6 and may be made of any suitable durable material, for example, a tool steel.

The drill guide 221 is similar to the guide 20 of FIGS. 1-6 except that the drill guide 221 includes drill openings 277 and does not include guide pegs 82 as in the guide 20 of FIGS. 1-6. The drill guide 221 of FIG. 22 includes a body 219 as well as a peripheral rim 230 extending around the periphery of the body 219. The peripheral rim 230 is preferably fitable within outer periphery groove 290 formed by the tool 222 as the tool 222 is moved about the outer periphery 221 of the cutting tool guide 220. (See FIG. 21).

Referring to FIGS. 22 and 23, the drill openings 277 are positioned in the body 219 of the drill guide 221 in a spaced apart relationship with as many drill openings 277 as reasonably can be placed in the body 219 while maintaining the necessary physical integrity of the drill guide 221. The drill openings 277 typically have a drill diameter DD which provides for cooperation with diameter DD of the drill 223. Preferably in order that a solitary drill 223 may be utilized, the drill openings 277 each have an identical drilled diameter DD.

Figure 11:
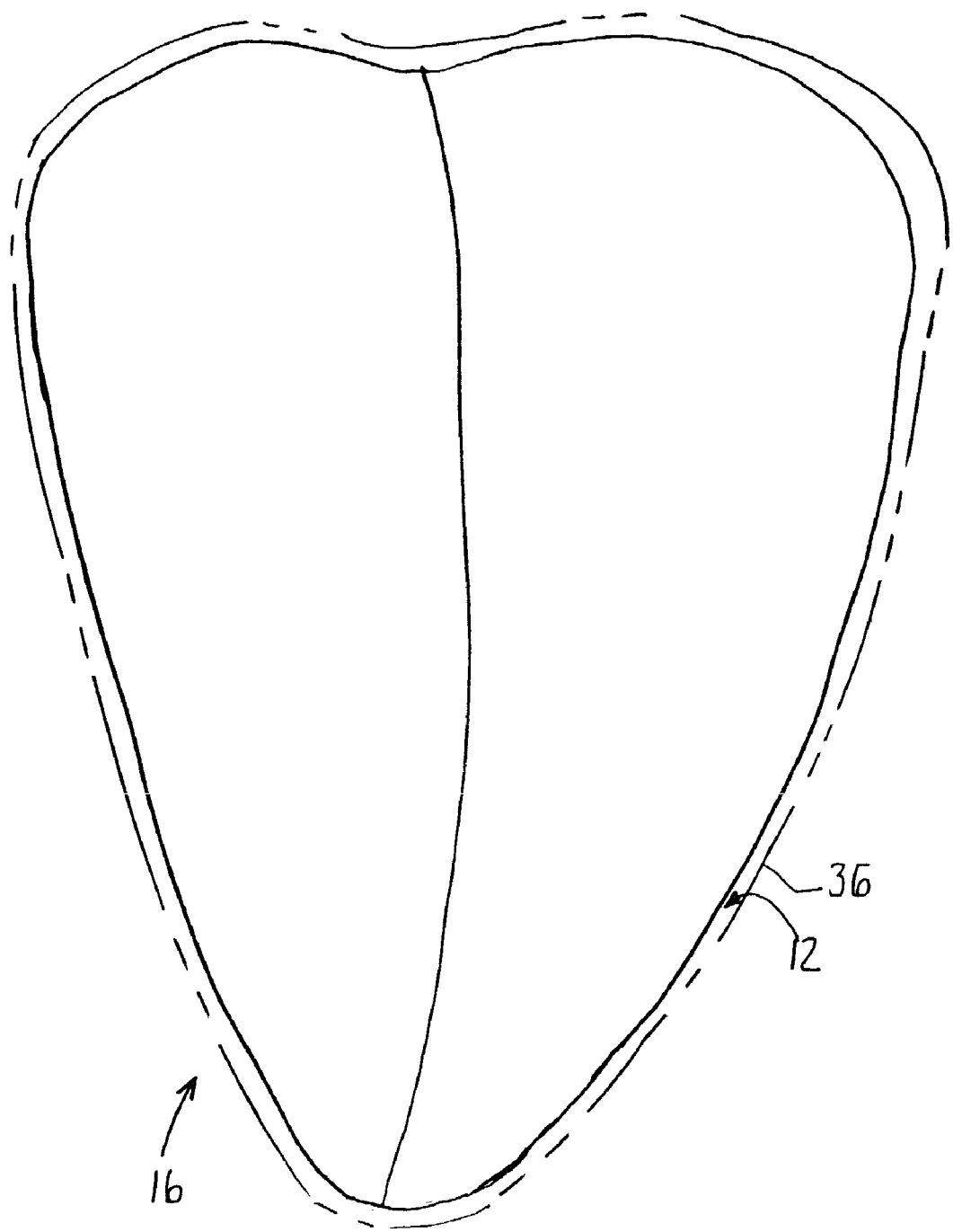
FIG. 11 is plan view of prosthesis for use in the bone cavity of FIG. 9.

Preferably, as is shown in FIGS. 22A and 23, the drill 223 has a drill length DL from the stop 255 of the drill 223 to the cutting edge 253 of the drill 223 which preferably is similar to the guide length GL from the upper surface 271 of the guide 221 through the face surface 273 of the cut in the femur for receiving the trochlear prosthesis 16 (see FIGS. 10-12). Preferably and as shown in FIG. 23, the upper surfaces 271 of the drill guides 221 are located on a plurality of planes such that the base surface 273 may be arcuate as shown in FIG. 23.

Figure 24:
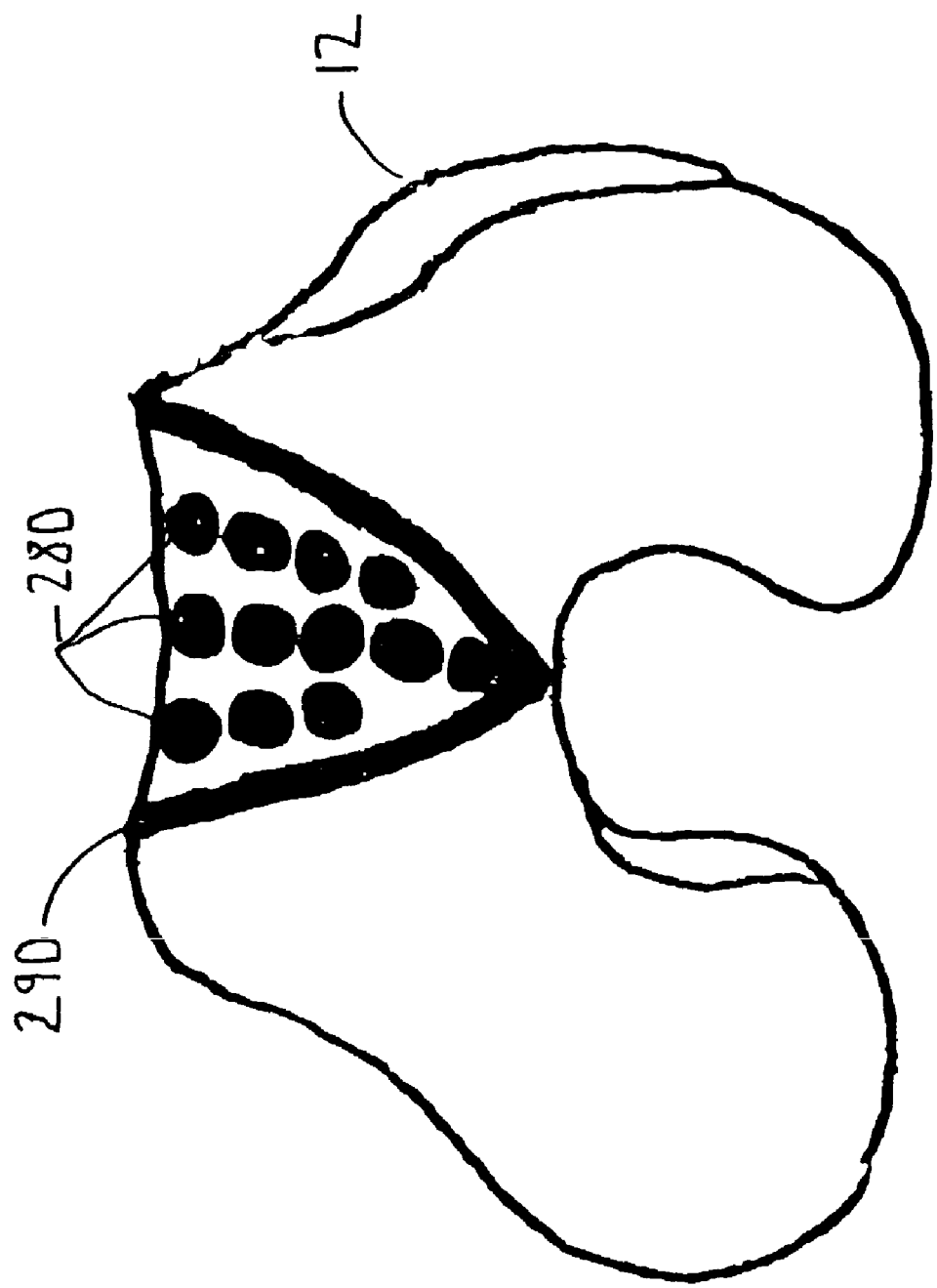
FIG. 24 is a portion plan view of the femur showing the cuts placed in the femur by the kit of FIGS. 21-23.

Referring now to FIG. 24, a femur 12 is shown with the peripheral groove 290 formed in the femur 12 as well as the drilled holes 280 which were placed in the femur 12 utilizing the drill guide 221 in cooperation with drill 223 of the FIGS. 22 and 22A, respectively. As can be seen from FIG. 24, the drilled holes 280 are positioned as close as reasonable can be obtained realizing the limits of the drill guide 221. As with the kit 10 of FIGS. 1-9, and as with the kit 110 of FIGS. 17 and 18, the kit 210, preferably includes a tool, for example, an osteotome, (not shown) which may be utilized to remove material between the drill holes 280 and the peripheral grooves 290 such that a cavity 14 similar to that is shown in FIG. 10 is formed in the femur 12. The cavity 14 is utilized to receive the prosthesis 16.

Figure 20:
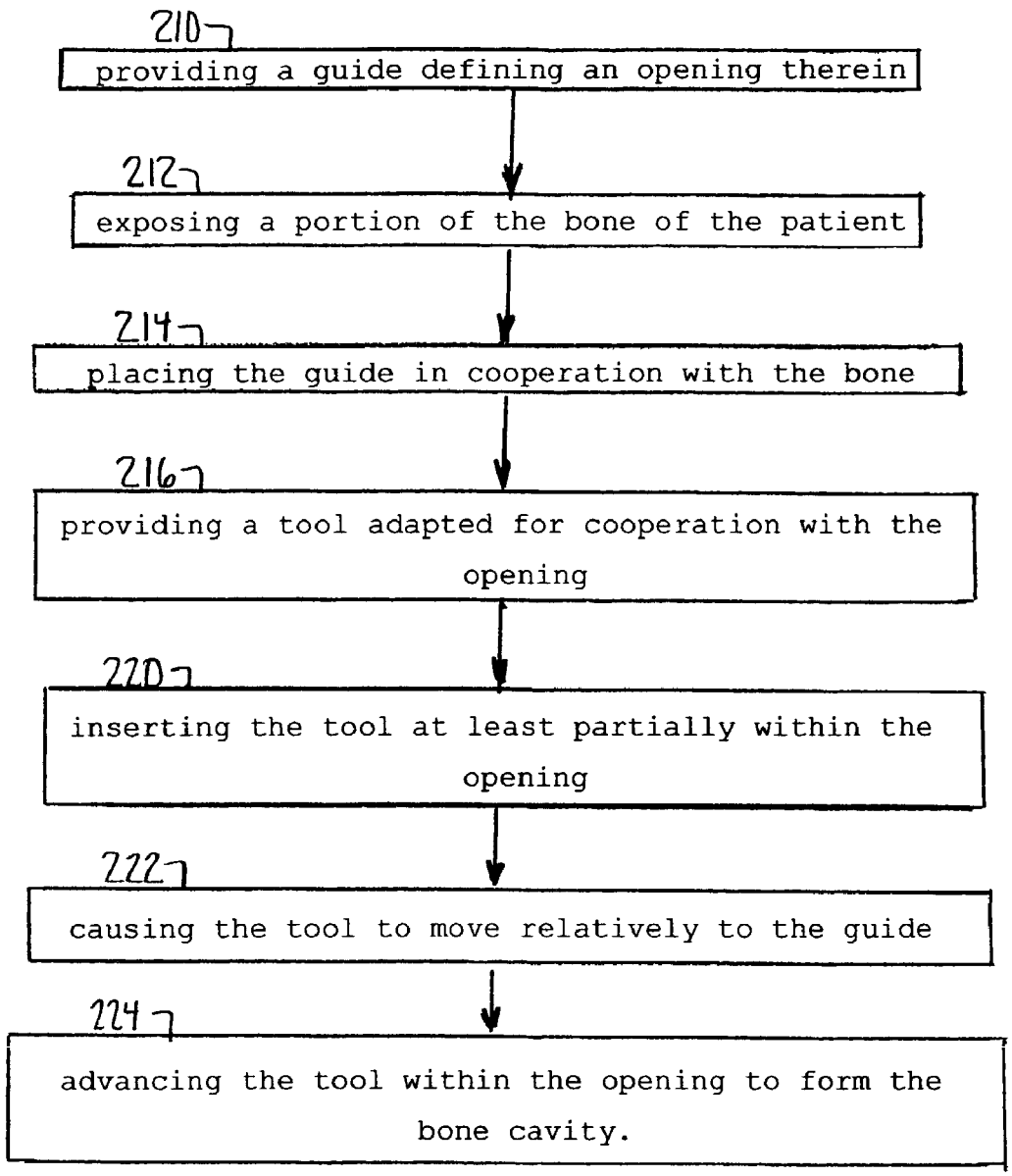
FIG. 20 is a flow diagram of a method of preparing a cavity for prosthesis according to the present invention.

Referring now to FIG. 20, a method for removal of bone from a patient to prepare a bone cavity for receiving prosthesis, is shown. The method includes a first step 210 of providing a guide for finding an opening in the guide. The method also includes a second step 212 of exposing a portion of the bone of the patient. The process further includes a third step 214 of placing the guide in cooperation with the patient. The method further includes a fourth step 216 of providing a tool adapted for cooperation with the opening. The method further includes a fifth step 220 of inserting the tool at least partially within the opening. The method further includes a sixth step 222 of causing the tool to move relatively to the guide. The method further includes a seventh step 224 of advancing the tool within the opening to form the bone cavity.

The step 224 of advancing the tool within the opening to form the bone cavity may include the steps of advancing the tool within the opening to form a portion of the bone cavity, providing a second tool and advancing the second tool within the opening to form the remainder of the bone cavity.

The method of removal of bone from a patient, according to the present invention, may be such that providing a tool step 216 may include advancing the tool within the opening to form a portion of the bone cavity; and the method may further include the steps of providing a second guide defining an opening in the second guide, placing the second guide in cooperation with the patient, inserting the tool at least partially within the opening, causing the tool to move relatively to the guide and advancing the tool within the opening to form the remainder of the bone cavity.

Although the present invention and its advantages have been described in detail, it should be understood that various changes, substitutions, and alterations can be made therein without departing from the spirit and scope of the present invention, as defined by the appended claims.

We claim:

1. An orthopaedic instrument for guiding a rotatable tool, comprising:
   a bone facing surface;
   a surface opposite the bone facing surface configured to limit movement of a portion of a rotatable tool in a direction toward the bone facing surface;
   a first guide wall extending from the bone facing surface to the surface opposite the bone facing surface and defining a first guide slot, the first guide slot including a first length and a first width, the first length substantially greater than the first width; and
   a second guide wall extending from the bone facing surface to the surface opposite the bone facing surface and defining a second guide slot, the second guide slot including a second length and a second width, the second length substantially greater than the second width, wherein a first portion of the second guide slot along the second length is located directly above an end portion of the first guide slot when the instrument is viewed in a plan view and a second portion of the second guide slot along the second length is located lower than the end portion of the first guide slot when the instrument is viewed in the plan view.

2. The instrument of claim 1, further comprising:
   a third guide wall extending from the bone facing surface to the surface opposite the bone facing surface and enclosing a third guide slot, the third guide slot having a first end portion proximate to the first guide slot and a second end portion proximate to the second guide slot.

3. The instrument of claim 2, further comprising:
   a fourth guide wall extending from the bone facing surface to the surface opposite the bone facing surface and enclosing a fourth guide slot, the fourth guide slot having a first end portion proximate to the first guide slot and a second end portion proximate to the second guide slot.

4. The instrument of claim 1, wherein the outer surface adjacent to the first guide slot has a contour along the entire first length substantially similar to a contour of a bearing surface of an associated implant.

5. The instrument of claim 4, wherein the outer surface adjacent to the second guide slot has a contour along the entire second length substantially similar to the contour of the bearing surface of the associated implant.

6. The instrument of claim 1, further comprising:
   a first peg extending from the bone facing surface in a direction away from the surface opposite the bone facing surface along a first axis.

7. The instrument of claim 6, further comprising:
a second peg extending from the bone facing surface in a direction away from the surface opposite the bone facing surface along a second axis, the second axis substantially parallel to the first axis.

8. An orthopaedic instrument for guiding a rotatable tool comprising:
a bone facing surface;
a surface opposite the bone facing surface configured to limit movement of a portion of a rotatable tool in a direction toward the bone facing surface;
a plurality of outer guide slots, each one of the plurality of outer guide slots including a guide wall extending from the bone facing surface to the surface opposite the bone facing surface and defining the respective one of the plurality of outer guide slots, and a first length and a first width, the first length substantially greater than the first width; and
a plurality of inner guide slots, each one of the plurality of inner guide slots including a guide wall extending from the bone facing surface to the surface opposite the bone facing surface and defining the respective one of the plurality of inner guide slots, and a second length and a second width, the second length substantially greater than the second width,
wherein the plurality of outer guide slots generally define a guide slot perimeter about the plurality of inner guide slots and at least one of the plurality of outer guide slots is sized and shaped differently from each of the plurality of inner guide slots.

9. The instrument of claim 8, wherein:
each of the plurality of outer guide slots extends lengthwise along the guide slot perimeter.

10. The instrument of claim 8, wherein:
the outer surface adjacent to each of the plurality of outer guide slots has a contour along the entire first length of each of the plurality of outer guide slots substantially similar to a contour of a bearing surface of an associated implant.

11. The instrument of claim 10, wherein:
the outer surface adjacent to each of the plurality of inner guide slots has a contour along the entire second length of each of the plurality of inner guide slots substantially similar to the contour of the bearing surface of the associated implant.

12. The instrument of claim 8, wherein the plurality of outer guide slots comprises three outer guide slots.

13. The instrument of claim 12, wherein the plurality of outer guide slots comprises four outer guide slots.

14. The instrument of claim 8, wherein the guide slot perimeter is shaped substantially similar to a perimeter of an associated implant.

15. An orthopaedic instrument for guiding a rotatable tool comprising:
an inner bone facing surface;
an outer surface opposite the inner bone facing surface;
a guide wall extending from the inner bone facing surface to the outer surface and defining a guide slot, the guide slot including a first length and a first width, the first length substantially greater than the first width, wherein the outer surface adjacent to the guide slot has a non-planar contour along the entire first length substantially similar to a non-planar contour of a bearing surface of an associated implant, and wherein the instrument includes a perimeter and the guide slot is one of a plurality of guide slots, and each of the plurality of guide slots extends lengthwise adjacent to the instrument perimeter.

16. The instrument of claim 15, wherein the plurality of guide slots substantially define a guide slot perimeter.

17. The instrument of claim 16, wherein the guide slot perimeter is shaped substantially similar to a perimeter of an associated implant.

18. The instrument of claim 15, wherein:
the plurality of guide slots include a plurality of outer guide slots, each of the plurality of outer guide slots including a first length and a first width, the first length substantially greater than the first width, wherein the outer surface has a contour along the entire first length of each of the plurality of outer guide slots substantially similar to the contour of the bearing surface of the associated implant.

19. The instrument of claim 18, further comprising:
a plurality of inner guide slots, each of the plurality of inner guide slots including a second length and a second width, the second length substantially greater than the second width, each of the plurality of inner guide slots having a first end portion proximate to a side portion of one of the plurality of outer guide slots and a second end portion proximate to a side portion of another of the plurality of outer guide slots.

20. The instrument of claim 19, wherein:
the contour of the outer surface along the entire second length of each of the plurality of inner guide slots is substantially similar to the contour of the bearing surface of the associated implant.

21. An orthopaedic instrument for guiding a rotatable tool comprising:
a non-planar bone facing surface configured to conform with a non-planar outer periphery of a bone;
a surface opposite the bone facing surface;
a plurality of outer guide slots, each one of the plurality of outer guide slots (i) including a guide wall extending from the bone facing surface to the surface opposite the bone facing surface, (ii) defining the respective one of the plurality of outer guide slots, and (iii) including a first length and a first width, the first length substantially greater than the first width, wherein the plurality of outer guide slots substantially define a periphery substantially similar to a periphery about a portion of an associated implant configured to replace a surface portion of the bone.

22. The instrument of claim 21, wherein each of the plurality of outer guide slots extends lengthwise along the periphery substantially defined by the plurality of outer guide slots.

23. The instrument of claim 21, wherein:
the outer surface has a contour along the entire first length of each of the plurality of outer guide slots substantially similar to a contour of a bearing surface of the associated implant.

24. The instrument of claim 23, further comprising:
a plurality of inner guide slots, each of the plurality of inner guide slots including a second length and a second width, the second length substantially greater than the second width, each of the plurality of inner guide slots having a first end portion proximate to a side portion of one of the plurality of outer guide slots and a second end portion proximate to a side portion of another of the plurality of outer guide slots.

25. The instrument of claim 24, wherein:
the contour of the outer surface along the entire second length of each of the plurality of inner guide slots is substantially similar to the contour of the bearing surface of the associated implant.

* * * * *